US008580529B2

(12) United States Patent
Danfelter et al.

(10) Patent No.: US 8,580,529 B2
(45) Date of Patent: Nov. 12, 2013

(54) DIAGNOSIS OF COLLAGEN IX DESTRUCTION

(75) Inventors: Mikael Danfelter, Hässelby (SE); Patrik Önnerfjord, Malmö (SE); Dick Heinegård, Lund (SE)

(73) Assignee: AnaMar AB, Gothenburg (SE)

( * ) Notice: Subject to any disclaimer, the term of this patent is extended or adjusted under 35 U.S.C. 154(b) by 46 days.

(21) Appl. No.: 12/928,884

(22) Filed: Dec. 22, 2010

(65) Prior Publication Data

US 2011/0144310 A1    Jun. 16, 2011

Related U.S. Application Data

(62) Division of application No. 12/072,428, filed on Feb. 26, 2008, now Pat. No. 7,892,768.

(60) Provisional application No. 60/904,684, filed on Mar. 2, 2007.

(51) Int. Cl.
*G01N 31/00* (2006.01)
*G01N 33/53* (2006.01)

(52) U.S. Cl.
USPC ............. 435/7.21; 435/2; 435/7.1; 436/501; 436/518; 422/430; 424/130.1; 530/300; 530/350

(58) Field of Classification Search
None
See application file for complete search history.

(56) References Cited

U.S. PATENT DOCUMENTS 7,745,391 B2 *  6/2010  Mintz et al. .................. 514/19.3
7,892,768 B2 *  2/2011  Danfelter et al. ............ 435/7.21

FOREIGN PATENT DOCUMENTS

| WO | WO 90/08195 | 7/1990 | |
|----|----|----|----|
| WO | WO 99/21011 | 4/1999 | |
| WO | WO 9921011 A1 * | 4/1999 | ........... G01N 33/564 |
| WO | WO 2004/110475 | 12/2004 | |

OTHER PUBLICATIONS

Aurich et al., Collagen and Proteoglycan Turnover in Focaly Damaged Human Ankle Cartilage, Arthritis & Rheumatism 54:244-252, 2006.
Hagg et al., Cartilage Fibrils of Mammals are Biochemically Heterogeneous: Differential Distribution of Decorin and Collagen IX, J. Cell Biol. 142:285-294, 1998.
Heathfield et al., Cleavage of Fibromodulin in Cartilage Explants Involves Removal of the N-terminal Tyrosine Sulfate-rich . . . , J. Biol. Chem. 279:6286-6295, 2004.
Johansson et al., Collagenase-3 (MMP-13) is Expressed by Hypertrophic Condrocytes, Periosteal Cells, and Osteoblasts . . . , Developmental Dynamics 208:387-397, 1997.
Kojima et al., Early Degradation of Type IX and Type II Collagen with the Onset of Experimental Inflammatory Arthritis, Arthritis & Rheumatism 44:120-127, 2001.
Mwale et al., Selective Assembly and Remodelling of Collagens II and IX Associated with Expression of the Condrocyte Hypertrophic . . . , Developmental Dynamics 218:648-662, 2000.
Thur et al., Mutations in Cartilage Oligomeric Matrix Protein Causing Pseudoachondroplasia and Multiple Epiphyseal . . . , J. Biol. Chem. 276:6083-6092, 2001.
Towbin et al., Electrophoretic transfer of proteins-from-polyacrylamide gels to nitrocellulose sheets: Procedure and . . . , Proc. Natl. Acad. Sci. 76:4350-4354, 1979.
Vasios et al., Cartilage Type IX Collagen-Proteoglycan Contains a Large Amino-terminal Globular Domain Encoded by Multiple.., J. Biol. Chem. 263:2324-2329, 1988.
Vaughan et al., D-Periodic Distribution of Collagen Type IX along Cartilage Fibrils, J. Cell Biol., 106:991-997, 1988.

* cited by examiner

*Primary Examiner* — Lisa Cook
(74) *Attorney, Agent, or Firm* — Lynn E. Barber

(57) ABSTRACT

A method for detecting or monitoring the presence of protein fragments, cleaved at novel cleaving sites near the N-terminal part of the collagen IX alpha 1 chain, close to the C-terminal part of the NC4 domain, and at the COL3 domain close to the NC3 domain. Neoepitope antibodies against the neoepitopes were created by the cleavages and an epitope in the cleaved N-terminal part of the NC4 domain unique to collagen IX. A diagnostic kit and antibodies useful in carrying out such methods are also presented.

2 Claims, 16 Drawing Sheets

Fig. 10

Human    P20849         RRETCHELPARITPS↓QTTDER 268

(SEQ ID NO: 16)

Bovine  119901059       RRETCNELPAR↑ITPGARSPGR 600

(SEQ ID NO: 17)

Fig. 11 A

| Protein | Start - End | M(expt)+H (Da) | Delta (Da) | Miss | Sequence | Modification |
|---|---|---|---|---|---|---|
| Collagen IX α1 | 381 - 399 | 2149.0860 | 0.0049 | 0 | R - IGQDDLPGFDLISQFQIDK – A (SEQ ID NO: 22) | |
| gi\|119901059 | 409 - 420 | 1235.7586 | 0.0593 | 0 | R - VVGSTALQVAYK - L (SEQ ID NO: 23) | |
| | 421 - 428 | 934.4733 | -0.0007 | 0 | K - LGNNVDFR - I (SEQ ID NO: 24) | |
| | 433 - 450 | 2184.1295 | 0.0536 | 0 | R - HLYPNGLPEEYSFLTTFR - M (SEQ ID NO: 25) | |
| | 459 - 471 | 1571.7896 | 0.0295 | 0 | K - HWSIWQIQDSSGK - E (SEQ ID NO: 26) | |
| | 515 - 521 | 817.4416 | -0.0184 | 0 | K - IMIGVER – S (SEQ ID NO: 27) | |
| | 515 - 521 | 833.4611 | 0.0062 | 0 | K - IMIGVER - S (SEQ ID NO: 27) | Oxidation (M) |
| | 522 - 532 | 1269.6286 | 0.0394 | 0 | R - SSATLFVDCNR – I (SEQ ID NO: 28) | |
| | 533 - 541 | 1052.6529 | 0.0067 | 0 | R - IESLPIKPR - G (SEQ ID NO: 29) | |
| | 542 - 554 | 1318.7367 | 0.0366 | 0 | R - GQIDVDGFAVLGK - L (SEQ ID NO: 30) | |
| | 555 - 580 | 3159.6834 | 0.0604 | 0 | K - LVDNPQVSVPFELQWMLIHCDPLRPR - R (SEQ ID NO: 31) | |
| | 581 - 590 | 1245.6484 | 0.0480 | 1 | R - RETCNELPAR - I (SEQ ID NO: 32) | |
| | 582 - 590 | 1089.5117 | 0.0124 | 0 | R - ETCNELPAR - I (SEQ ID NO:1) | |

Fig 11 B

| Protein | Start - End | M(expt)+H (Da) | Delta (Da) | Miss | Sequence | Modifications |
|---|---|---|---|---|---|---|
| Collagen IX α1 | 381 - 399 | 2149.0944 | 0.0132 | 0 | R - IGQDDLPGFDLISQFQIDK – A (SEQ ID NO: 22) | |
| Gi\|119901059 | 409 - 420 | 1235.7126 | 0.0133 | 0 | R – VVGSTALQVAYK – L (SEQ ID NO: 23) | |
| | 421 - 428 | 934.4421 | -0.0319 | 0 | K - LGNNVDFR – I (SEQ ID NO: 24) | |
| | 421 - 432 | 1401.7979 | 0.0383 | 1 | K - LGNNVDFRIPTR – H (SEQ ID NO: 33) | |
| | 433 - 450 | 2184.0906 | 0.0147 | 0 | R - HLYPNGLPEEYSFLTTFR – M (SEQ ID NO: 25) | |
| | 484 - 490 | 817.4028 | -0.0062 | 0 | K - SVSFSYK – G (SEQ ID NO: 34) | |
| | 515 - 521 | 833.4282 | -0.0267 | 0 | K - IMIGVER - S (SEQ ID NO: 27) | Oxidation (M) |
| | 522 - 532 | 1269.6242 | 0.0350 | 0 | R - SSATLFVDCNR – I (SEQ ID NO: 28) | |
| | 522 - 541 | 2303.2310 | 0.0135 | 1 | R - SSATLFVDCNRIESLPIKPR – G (SEQ ID NO: 35) | |
| | 533 - 541 | 1052.6380 | -0.0082 | 0 | R - IESLPIKPR - G (SEQ ID NO: 29) | |
| | 542 - 554 | 1318.7246 | 0.0245 | 0 | R - GQIDVDGFAVLGK – L (SEQ ID NO: 30) | |
| | 581 - 590 | 1245.6310 | 0.0306 | 1 | R - RETCNELPAR – I (SEQ ID NO: 32) | |
| | 582 - 590 | 1089.5001 | 0.0008 | 0 | R - ETCNELPAR – I (SEQ ID NO: 1) | |
| | 601 - 630 | 2819.4455 | 0.0861 | 1 | R - GPPGEQGPPGPPGPPGVPGIDGIDGDRGPK - G (SEQ ID NO: 36) | 3 Hydroxylation (P) |
| | 601 - 630 | 2835.3742 | 0.0199 | 1 | R - GPPGEQGPPGPPGPPGVPGIDGIDGDRGPK - G (SEQ ID NO: 36) | 4 Hydroxylation (P) |
| | 601 - 630 | 2851.3719 | 0.0227 | 1 | R - GPPGEQGPPGPPGPPGVPGIDGIDGDRGPK - G (SEQ ID NO: 36) | 5 Hydroxylation (P) |
| | 631 - 672 | 3757.7917 | -0.0134 | 0 | K - GPPGPPGPPGEPGKPGAPGKPGTPGADGLTGPDGSPGSVGPR - G (SEQ ID NO: 37) | 5 Hydroxylation (P) |
| | 631 - 672 | 3773.9272 | 0.1272 | 0 | K - GPPGPPGPPGEPGKPGAPGKPGTPGADGLTGPDGSPGSVGPR - G (SEQ ID NO: 37) | 6 Hydroxylation (P) |
| | 690 - 709 | 1800.9658 | 0.0420 | 0 | R - GIPGPPGPPGGAGLPGELGR - V (SEQ ID NO: 38) | 3 Hydroxylation (P) |
| | 690 - 709 | 1816.9402 | 0.0215 | 0 | R - GIPGPPGPPGGAGLPGELGR - V (SEQ ID NO: 38) | 4 Hydroxylation (P) |
| | 690 - 709 | 1832.9246 | 0.0110 | 0 | R - GIPGPPGPPGGAGLPGELGR - V (SEQ ID NO: 38) | 5 Hydroxylation (P) |
| | 710 - 718 | 855.4324 | -0.0246 | 0 | R - VGPIGDPGK - R (SEQ ID NO: 39) | Hydroxylation (P) |
| | 710 - 719 | 1011.5376 | -0.0205 | 1 | R - VGPIGDPGKR - G (SEQ ID NO: 39) | Hydroxylation (P) |

Fig 11 C

| Protein | Start - End | $M_{(expt)}$+H (Da) | Delta (Da) | Miss | Sequence | Modification |
|---|---|---|---|---|---|---|
| Collagen IX α1 gi\|11990105 9 | 381 - 399 | 2149.0553 | -0.0258 | 0 | R - IGQDDLPGFDLISQFQIDK – A (SEQ ID NO: 22) | |
| | 409 - 420 | 1235.7345 | 0.0352 | 0 | R - VVGSTALQVAYK – L (SEQ ID NO: 23) | |
| | 421 - 428 | 934.4945 | 0.0204 | 0 | K - LGNNVDFR – I (SEQ ID NO: 24) | |
| | 433 - 450 | 2184.0526 | -0.0234 | 0 | R - HLYPNGLPEEYSFLTTFR – M (SEQ ID NO: 25) | |
| | 515 - 521 | 817.4383 | -0.0217 | 0 | K - IMIGVER – S (SEQ ID NO: 27) | |
| | 522 - 532 | 1269.6251 | 0.0360 | 0 | R - SSATLFVDCNR – I (SEQ ID NO: 28) | |
| | 533 - 541 | 1052.6653 | 0.0191 | 0 | R - IESLPIKPR – G (SEQ ID NO: 29) | |
| | 542 - 554 | 1318.7353 | 0.0353 | 0 | R - GQIDVDGFAVLGK – L (SEQ ID NO: 30) | |
| | 581 - 590 | 1245.6500 | 0.0496 | 1 | R - RETCNELPAR – I (SEQ ID NO: 32) | |
| | 582 - 590 | 1089.5213 | 0.0220 | 0 | R - ETCNELPAR – I (SEQ ID NO:1) | |
| | 601 - 630 | 2787.3338 | -0.0358 | 1 | R - GPPGEQGPPGPPGPPGVPGIDGIDGDRGPK - G (SEQ ID NO: 36) | Hydroxylation (P) |
| | 601 - 630 | 2819.3611 | 0.0017 | 1 | R - GPPGEQGPPGPPGPPGVPGIDGIDGDRGPK - G (SEQ ID NO: 36) | 3 Hydroxylation (P) |
| | 601 - 630 | 2835.3430 | -0.0113 | 1 | R - GPPGEQGPPGPPGPPGVPGIDGIDGDRGPK - G (SEQ ID NO: 36) | 4 Hydroxylation (P) |
| | 601 - 630 | 2851.3430 | -0.0062 | 1 | R - GPPGEQGPPGPPGPPGVPGIDGIDGDRGPK - G (SEQ ID NO: 36) | 5 Hydroxylation (P) |
| | 690 - 709 | 1800.9159 | -0.0079 | 0 | R - GIPGPPGPPGGAGLPGELGR - V (SEQ ID NO: 38) | 3 Hydroxylation (P) |
| | 690 - 709 | 1816.8818 | -0.0369 | 0 | R - GIPGPPGPPGGAGLPGELGR - V (SEQ ID NO: 38) | 4 Hydroxylation (P) |
| | 690 - 709 | 1832.8561 | -0.0575 | 0 | R - GIPGPPGPPGGAGLPGELGR - V (SEQ ID NO: 38) | 5 Hydroxylation (P) |
| | 719 - 751 | 3352.5827 | 0.0606 | 1 | K - RGPPGPPGPPGPSGTIGFHDGDPLCPNSCPPGR – S (SEQ ID NO: 40) | 3 Hydroxylation (P) |
| | 720 - 751 | 3196.4349 | 0.0139 | 0 | R - GPPGPPGPPGPSGTIGFHDGDPLCPNSCPPGR - S (SEQ ID NO: 41) | 3 Hydroxylation (P) |
| | 752 - 761 | 1066.5215 | 0.0229 | 0 | R – SGYPGLPGMR - G (SEQ ID NO: 42) | 2 Hydroxylation (P) |
| | 752 - 761 | 1082.5136 | 0.0202 | 0 | R – SGYPGLPGMR - G (SEQ ID NO: 42) | Oxidation (M); 2 Hydroxylation (P) |
| | 819 - 839 | 2034.9144 | -0.0330 | 0 | R - GLDGEPGPQGLPGAPGDQGQR – G (SEQ ID NO: 43) | 2 Hydroxylation (P) |
| | 819 - 839 | 2050.9366 | -0.0058 | 0 | R - GLDGEPGPQGLPGAPGDQGQR – G (SEQ ID NO: 43) | 3 Hydroxylation (P) |
| | 840 - 851 | 1179.6454 | 0.0338 | 1 | R - GPPGEIGPKGDR – G (SEQ ID NO: 44) | |
| | 852 - 877 | 2415.2194 | -0.0067 | 1 | R - GPQGSPGIPGLPGPKGDTGLPGVDGR - D (SEQ ID NO: 45) | 2 Hydroxylation (P) |
| | 960 - 973 | 1276.6582 | 0.0051 | 0 | R – GEVGPVGPPGPPGK – L (SEQ ID NO: 46) | 2 Hydroxylation (P) |

Fig.12 A

| protein | Start - End | M(expt) | Delta (Da) | Miss | Sequence | Ion score |
|---|---|---|---|---|---|---|
| gi|19901059 | 457 - 466 | 1353.6852 | 0.0023 | 0 | L - EKHWSIWQIQ - D (SEQ ID NO: 47) | 8 |
| | 547 - 556 | 1017.5858 | 0.0000 | 0 | V - DGFAVLGKLV - D (SEQ ID NO: 48) | 13 |
| | 557 - 574 | 2212.0394 | -0.0050 | 1 | V - DNPQVSVPFELQWMLIHC - D (SEQ ID NO: 49) | 13 |
| | 566 - 574 | 1228.5726 | -0.0006 | 0 | F - ELQWMLIHC - D (SEQ ID NO: 50) | 24 |

Fig 12 B

| Protein | Start - End | M(expt) | Delta (Da) | Miss | Sequence | Ion score |
|---|---|---|---|---|---|---|
| gi|19901059 | 582 - 590 | 1088.4938 | 0.0018 | 0 | R - ETCNELPAR - I (SEQ ID NO: 1) | 43 |

Fig 12 C

| Protein | Start - End | M(expt) | Delta (Da) | Miss | Sequence | Modifications | Ion score |
|---|---|---|---|---|---|---|---|
| gi|19901059 | 363 - 378 | 1806.7726 | -0.0003 | 0 | R - FPVNSNSNGENELCPK - V (SEQ ID NO: 51) | 2 Deamidation (NQ) | 13 |
| | 365 - 378 | 1562.6468 | -0.0049 | 0 | P - VNSNSNGENELCPK - V (SEQ ID NO: 52) | 2 Deamidation (NQ) | 11 |
| | 367 - 378 | 1348.5562 | -0.0002 | 0 | N - SNSNGENELCPK - V. (SEQ ID NO: 53) | Deamidation (NQ) | 63 |
| | 381 - 399 | 2148.0814 | 0.0076 | 0 | R - IGQDDLPGFDLISQFQIDK - A (SEQ ID NO: 22) | | 41 |
| | 409 - 420 | 1234.6974 | 0.0054 | 0 | R - VVGSTALQVAYK - L (SEQ ID NO: 23) | | 90 |
| | 421 - 428 | 933.4652 | -0.0015 | 0 | K - LGNNVDFR - I (SEQ ID NO: 24) | | 56 |
| | 421 - 428 | 934.4522 | 0.0015 | 0 | K - LGNNVDFR - I (SEQ ID NO: 24) | Deamidation (NQ) | 22 |
| | 433 - 450 | 2184.0481 | -0.0046 | 0 | R - HLYPNGLPEEYSFLTTFR - M (SEQ ID NO: 25) | Deamidation (NQ) | 13 |
| | 459 - 471 | 1570.7518 | -0.0010 | 0 | K - HWSIWQIQDSSGK - E (SEQ ID NO: 26) | | 65 |
| | 491 - 514 | 2618.2705 | -0.0060 | 0 | K - GLDGSLQTAAFSNLPSLFDSQWHK - I (SEQ ID NO: 54) | | 52 |
| | 533 - 541 | 1051.6430 | 0.0041 | 0 | R - IESLPIKPR - G (SEQ ID NO: 29) | | 54 |
| | 542 - 554 | 1317.6970 | 0.0043 | 0 | R - GQIDVDGFAVLGK - L (SEQ ID NO: 30) | | 67 |
| | 581 - 590 | 1244.5958 | 0.0027 | 1 | R - RETCNELPAR - I (SEQ ID NO: 32) | | 27 |
| | 582 - 590 | 1088.4734 | -0.0186 | 0 | R - ETCNELPAR - I (SEQ ID NO: 1) | | 48 |

Fig.13

| Protein | Start - End | M(expt) | Delta (Da) | Miss | Sequence | Modification | Ion score |
|---|---|---|---|---|---|---|---|
| gi\|1990105 9 | 381 - 399 | 2148.0514 | -0.0224 | 0 | R - IGQDDLPGFDLISQFQIDK - A (SEQ ID NO: 22) | | 84 |
| | 381 - 399 | 2148.8932 | -0.1647 | 0 | R - IGQDDLPGFDLISQFQIDK - A (SEQ ID NO: 22) | Deamidation (NQ) | 21 |
| | 405 - 419 | 1576.6094 | -0.2365 | 1 | R - AIQRVVGSTALQVAY - K (SEQ ID NO: 55) | 2 Deamidation (NQ) | 4 |
| | 409 - 420 | 1234.7914 | 0.0994 | 0 | R - VVGSTALQVAYK - L (SEQ ID NO: 23) | | 62 |
| | 433 - 450 | 2184.0082 | -0.0445 | 0 | R - HLYPNGLPEEYSFLTTFR - M (SEQ ID NO: 25) | Deamidation (NQ) | 76 |
| | 522 - 532 | 1268.6014 | 0.0195 | 0 | R - SSATLFVDCNR - I (SEQ ID NO: 28) | | 55 |
| | 581 - 590 | 1244.7394 | 0.1463 | 1 | R - RETCNELPAR - I (SEQ ID NO: 32) | | 38 |
| | 719 - 732 | 1273.6574 | 0.0524 | 1 | K - RGPPGPPGPPGPSG - T (SEQ ID NO: 3) | 3 Hydroxylation (P) | 53 |

Fig.14

| Protein | Start - End | M(expt) | Delta (Da) | Miss | Sequence | Modifications | Ion score |
|---|---|---|---|---|---|---|---|
| | 42 – 51 | 607.4550 | 0.2306 | 0 | N - ELCPKIRIGQ - D (SEQ ID NO: 56) | | 12 |
| | 58 – 65 | 475.2800 | 0.0538 | 0 | F - DLISQFQV – D (SEQ ID NO: 57) | | 34 |
| | 213 – 224 | 609.9730 | 0.2659 | 1 | I - DIDGFAVLGKLA - D (SEQ ID NO: 58) | | 76 |
| | 215 – 224 | 495.9670 | 0.3649 | 0 | I - DGFAVLGKLA – D (SEQ ID NO: 59) | | 38 |
| | 225 – 233 | 501.8790 | 0.2617 | 0 | A - DNPQVSVPF - E (SEQ ID NO: 60) | | 40 |
| | 225 – 242 | 738.3790 | 0.0707 | 1 | A - DNPQVSVPFELQWMLIHC – D (SEQ ID NO: 61) | | 31 |
| | 234 – 242 | 615.3340 | 0.0802 | 0 | F - ELQWMLIHC – D (SEQ ID NO: 62) | | 52 |
| | 234 – 242 | 623.4080 | 0.2333 | 0 | F - ELQWMLIHC – D (SEQ ID NO: 62) | Oxidation (M) | 46 |

Fig.15

| amino acids | sequence | m/z (charge: +2) | missed cleavage | $R_T$ | Cleavage site/control |
|---|---|---|---|---|---|
| 254-263 | ELPARITPSQ (SEQ ID NO: 18) | 556.3095 | 0 | 24.5-24.7 | novel |
| 250-263 | ETCHELPARITPSQ (SEQ ID NO: 11) | 819.8995 | 1 | 24.2-24.5 | novel |
| 58-65 | DLIQFQV (SEQ ID NO: 19) | 475.2460 | 0 | 38.2-38.4 | control |
| 213-224 | DIDGFAVLGKLA (SEQ ID NO: 20) | 609.8330 | 1 | 40.1-40.2 | control |
| 250-258 | ETCHELPAR (SEQ ID NO: 21) | 556.7620 | 1 | unknown | bovine |

SEQUENCE LISTING

```
<160> NUMBER OF SEQ ID NOS: 62

<210> SEQ ID NO 1
<211> LENGTH: 9
<212> TYPE: PRT
<213> ORGANISM: Bovine

<400> SEQUENCE: 1

Glu Thr Cys Asn Glu Leu Pro Ala Arg
1               5

<210> SEQ ID NO 2
<211> LENGTH: 8
<212> TYPE: PRT
<213> ORGANISM: Bovine

<400> SEQUENCE: 2

Ile Thr Pro Gly Ala Arg Ser Pro
1               5

<210> SEQ ID NO 3
<211> LENGTH: 14
<212> TYPE: PRT
<213> ORGANISM: Bovine

<400> SEQUENCE: 3

Arg Gly Pro Pro Gly Pro Pro Gly Pro Pro Gly Pro Ser Gly
1               5                   10

<210> SEQ ID NO 4
<211> LENGTH: 8
<212> TYPE: PRT
<213> ORGANISM: Bovine

<400> SEQUENCE: 4

Thr Ile Gly Phe His Asp Gly Asp
1               5
```

-continued

```
<210> SEQ ID NO 5
<211> LENGTH: 20
<212> TYPE: PRT
<213> ORGANISM: Human

<400> SEQUENCE: 5

Cys His Glu Leu Pro Ala Arg Ile Thr Pro Ser Gln Thr Thr Asp Glu
1               5                   10                  15

Arg Gly Pro Pro
            20

<210> SEQ ID NO 6
<211> LENGTH: 12
<212> TYPE: PRT
<213> ORGANISM: Human

<400> SEQUENCE: 6

Cys His Glu Leu Pro Ala Arg Ile Thr Pro Ser Gln
1               5                   10

<210> SEQ ID NO 7
<211> LENGTH: 8
<212> TYPE: PRT
<213> ORGANISM: Human

<400> SEQUENCE: 7

Thr Thr Asp Glu Arg Gly Pro Pro
1               5

<210> SEQ ID NO 8
<211> LENGTH: 22
<212> TYPE: PRT
<213> ORGANISM: Human

<400> SEQUENCE: 8

Arg Gly Pro Pro Gly Pro Pro Gly Pro Pro Gly Pro Arg Gly Thr Ile
1               5                   10                  15

Gly Phe His Asp Gly Asp
            20

<210> SEQ ID NO 9
<211> LENGTH: 14
<212> TYPE: PRT
<213> ORGANISM: Human

<400> SEQUENCE: 9

Arg Gly Pro Pro Gly Pro Pro Gly Pro Pro Gly Pro Arg Gly
1               5                   10

<210> SEQ ID NO 10
<211> LENGTH: 8
<212> TYPE: PRT
<213> ORGANISM: Human

<400> SEQUENCE: 10

Thr Ile Gly Phe His Asp Gly Asp
1               5

<210> SEQ ID NO 11
<211> LENGTH: 14
<212> TYPE: PRT
<213> ORGANISM: Human

<400> SEQUENCE: 11

Glu Thr Cys His Glu Leu Pro Ala Arg Ile Thr Pro Ser Gln
```

<210> SEQ ID NO 12
<211> LENGTH: 12
<212> TYPE: PRT
<213> ORGANISM: Human

<400> SEQUENCE: 12

Ser Asn Ser Asp Gly Glu Asn Glu Leu Cys Pro Lys
1               5                   10

<210> SEQ ID NO 13
<211> LENGTH: 8
<212> TYPE: PRT
<213> ORGANISM: Human

<400> SEQUENCE: 13

Pro Ala Arg Ile Thr Pro Ser Gln
1               5

<210> SEQ ID NO 14
<211> LENGTH: 16
<212> TYPE: PRT
<213> ORGANISM: Human

<400> SEQUENCE: 14

Cys Gly Gln Asp Asp Leu Pro Gly Phe Asp Leu Ile Ser Gln Phe Gln
1               5                   10                  15

<210> SEQ ID NO 15
<211> LENGTH: 11
<212> TYPE: PRT
<213> ORGANISM: Human

<400> SEQUENCE: 15

Gly Gly Gly Pro Ala Arg Ile Thr Pro Ser Gln
1               5                   10

<210> SEQ ID NO 16
<211> LENGTH: 21
<212> TYPE: PRT
<213> ORGANISM: Human

<400> SEQUENCE: 16

Arg Arg Glu Thr Cys His Glu Leu Pro Ala Arg Ile Thr Pro Ser Gln
1               5                   10                  15

Thr Thr Asp Glu Arg
            20

<210> SEQ ID NO 17
<211> LENGTH: 21
<212> TYPE: PRT
<213> ORGANISM: Bovine

<400> SEQUENCE: 17

Arg Arg Glu Thr Cys Asn Glu Leu Pro Ala Arg Ile Thr Pro Gly Ala
1               5                   10                  15

Arg Ser Pro Gly Arg
            20

<210> SEQ ID NO 18
<211> LENGTH: 10
<212> TYPE: PRT
<213> ORGANISM: Human

-continued

<400> SEQUENCE: 18

Glu Leu Pro Ala Arg Ile Thr Pro Ser Gln
1               5                   10

<210> SEQ ID NO 19
<211> LENGTH: 7
<212> TYPE: PRT
<213> ORGANISM: Human

<400> SEQUENCE: 19

Asp Leu Ile Gln Phe Gln Val
1               5

<210> SEQ ID NO 20
<211> LENGTH: 12
<212> TYPE: PRT
<213> ORGANISM: Human

<400> SEQUENCE: 20

Asp Ile Asp Gly Phe Ala Val Leu Gly Lys Leu Ala
1               5                   10

<210> SEQ ID NO 21
<211> LENGTH: 9
<212> TYPE: PRT
<213> ORGANISM: Human

<400> SEQUENCE: 21

Glu Thr Cys His Glu Leu Pro Ala Arg
1               5

<210> SEQ ID NO 22
<211> LENGTH: 19
<212> TYPE: PRT
<213> ORGANISM: Bovine

<400> SEQUENCE: 22

Ile Gly Gln Asp Asp Leu Pro Gly Phe Asp Leu Ile Ser Gln Phe Gln
1               5                   10                  15

Ile Asp Lys

<210> SEQ ID NO 23
<211> LENGTH: 12
<212> TYPE: PRT
<213> ORGANISM: Bovine

<400> SEQUENCE: 23

Val Val Gly Ser Thr Ala Leu Gln Val Ala Tyr Lys
1               5                   10

<210> SEQ ID NO 24
<211> LENGTH: 8
<212> TYPE: PRT
<213> ORGANISM: Bovine

<400> SEQUENCE: 24

Leu Gly Asn Asn Val Asp Phe Arg
1               5

<210> SEQ ID NO 25
<211> LENGTH: 18
<212> TYPE: PRT
<213> ORGANISM: Bovine

<400> SEQUENCE: 25

His Leu Tyr Pro Asn Gly Leu Pro Glu Glu Tyr Ser Phe Leu Thr Thr
1               5                   10                  15

Phe Arg

<210> SEQ ID NO 26
<211> LENGTH: 13
<212> TYPE: PRT
<213> ORGANISM: Bovine

<400> SEQUENCE: 26

His Trp Ser Ile Trp Gln Ile Gln Asp Ser Ser Gly Lys
1               5                   10

<210> SEQ ID NO 27
<211> LENGTH: 7
<212> TYPE: PRT
<213> ORGANISM: Bovine

<400> SEQUENCE: 27

Ile Met Ile Gly Val Glu Arg
1               5

<210> SEQ ID NO 28
<211> LENGTH: 11
<212> TYPE: PRT
<213> ORGANISM: Bovine

<400> SEQUENCE: 28

Ser Ser Ala Thr Leu Phe Val Asp Cys Asn Arg
1               5                   10

<210> SEQ ID NO 29
<211> LENGTH: 9
<212> TYPE: PRT
<213> ORGANISM: Bovine

<400> SEQUENCE: 29

Ile Glu Ser Leu Pro Ile Lys Pro Arg
1               5

<210> SEQ ID NO 30
<211> LENGTH: 13
<212> TYPE: PRT
<213> ORGANISM: Bovine

<400> SEQUENCE: 30

Gly Gln Ile Asp Val Asp Gly Phe Ala Val Leu Gly Lys
1               5                   10

<210> SEQ ID NO 31
<211> LENGTH: 26
<212> TYPE: PRT
<213> ORGANISM: Bovine

<400> SEQUENCE: 31

Leu Val Asp Asn Pro Gln Val Ser Val Pro Phe Glu Leu Gln Trp Met
1               5                   10                  15

Leu Ile His Cys Asp Pro Leu Arg Pro Arg
            20                  25

<210> SEQ ID NO 32
<211> LENGTH: 10
<212> TYPE: PRT
<213> ORGANISM: Bovine

```
<400> SEQUENCE: 32

Arg Glu Thr Cys Asn Glu Leu Pro Ala Arg
1               5                  10

<210> SEQ ID NO 33
<211> LENGTH: 12
<212> TYPE: PRT
<213> ORGANISM: Bovine

<400> SEQUENCE: 33

Leu Gly Asn Asn Val Asp Phe Arg Ile Pro Thr Arg
1               5                  10

<210> SEQ ID NO 34
<211> LENGTH: 7
<212> TYPE: PRT
<213> ORGANISM: Bovine

<400> SEQUENCE: 34

Ser Val Ser Phe Ser Tyr Lys
1               5

<210> SEQ ID NO 35
<211> LENGTH: 20
<212> TYPE: PRT
<213> ORGANISM: Bovine

<400> SEQUENCE: 35

Ser Ser Ala Thr Leu Phe Val Asp Cys Asn Arg Ile Glu Ser Leu Pro
1               5                  10                  15

Ile Lys Pro Arg
            20

<210> SEQ ID NO 36
<211> LENGTH: 30
<212> TYPE: PRT
<213> ORGANISM: Bovine

<400> SEQUENCE: 36

Gly Pro Pro Gly Glu Gln Gly Pro Gly Pro Gly Pro Pro Gly
1               5                  10                  15

Val Pro Gly Ile Asp Gly Ile Asp Gly Asp Arg Gly Pro Lys
            20                  25                  30

<210> SEQ ID NO 37
<211> LENGTH: 42
<212> TYPE: PRT
<213> ORGANISM: Bovine

<400> SEQUENCE: 37

Gly Pro Pro Gly Pro Pro Gly Pro Gly Glu Pro Gly Lys Pro Gly
1               5                  10                  15

Ala Pro Gly Lys Pro Gly Thr Pro Gly Ala Asp Gly Leu Thr Gly Pro
            20                  25                  30

Asp Gly Ser Pro Gly Ser Val Gly Pro Arg
            35                  40

<210> SEQ ID NO 38
<211> LENGTH: 20
<212> TYPE: PRT
<213> ORGANISM: Bovine

<400> SEQUENCE: 38
```

-continued

Gly Ile Pro Gly Pro Gly Pro Gly Gly Ala Gly Leu Pro Gly
1               5                   10                  15

Glu Leu Gly Arg
            20

<210> SEQ ID NO 39
<211> LENGTH: 9
<212> TYPE: PRT
<213> ORGANISM: Bovine

<400> SEQUENCE: 39

Val Gly Pro Ile Gly Asp Pro Gly Lys
1               5

<210> SEQ ID NO 40
<211> LENGTH: 33
<212> TYPE: PRT
<213> ORGANISM: Bovine

<400> SEQUENCE: 40

Arg Gly Pro Pro Gly Pro Pro Gly Pro Pro Gly Pro Ser Gly Thr Ile
1               5                   10                  15

Gly Phe His Asp Gly Asp Pro Leu Cys Pro Asn Ser Cys Pro Pro Gly
            20                  25                  30

Arg

<210> SEQ ID NO 41
<211> LENGTH: 32
<212> TYPE: PRT
<213> ORGANISM: Bovine

<400> SEQUENCE: 41

Gly Pro Pro Gly Pro Pro Gly Pro Pro Gly Pro Ser Gly Thr Ile Gly
1               5                   10                  15

Phe His Asp Gly Asp Pro Leu Cys Pro Asn Ser Cys Pro Pro Gly Arg
            20                  25                  30

<210> SEQ ID NO 42
<211> LENGTH: 10
<212> TYPE: PRT
<213> ORGANISM: Bovine

<400> SEQUENCE: 42

Ser Gly Tyr Pro Gly Leu Pro Gly Met Arg
1               5                   10

<210> SEQ ID NO 43
<211> LENGTH: 21
<212> TYPE: PRT
<213> ORGANISM: Bovine

<400> SEQUENCE: 43

Gly Leu Asp Gly Glu Pro Gly Pro Gln Gly Leu Pro Gly Ala Pro Gly
1               5                   10                  15

Asp Gln Gly Gln Arg
            20

<210> SEQ ID NO 44
<211> LENGTH: 12
<212> TYPE: PRT
<213> ORGANISM: Bovine

<400> SEQUENCE: 44

```
Gly Pro Pro Gly Glu Ile Gly Pro Lys Gly Asp Arg
1               5                   10

<210> SEQ ID NO 45
<211> LENGTH: 26
<212> TYPE: PRT
<213> ORGANISM: Bovine

<400> SEQUENCE: 45

Gly Pro Gln Gly Ser Pro Gly Ile Pro Gly Leu Pro Gly Pro Lys Gly
1               5                   10                  15

Asp Thr Gly Leu Pro Gly Val Asp Gly Arg
            20                  25

<210> SEQ ID NO 46
<211> LENGTH: 14
<212> TYPE: PRT
<213> ORGANISM: Bovine

<400> SEQUENCE: 46

Gly Glu Val Gly Pro Val Gly Pro Pro Gly Pro Pro Gly Lys
1               5                   10

<210> SEQ ID NO 47
<211> LENGTH: 10
<212> TYPE: PRT
<213> ORGANISM: Bovine

<400> SEQUENCE: 47

Glu Lys His Trp Ser Ile Trp Gln Ile Gln
1               5                   10

<210> SEQ ID NO 48
<211> LENGTH: 10
<212> TYPE: PRT
<213> ORGANISM: Bovine

<400> SEQUENCE: 48

Asp Gly Phe Ala Val Leu Gly Lys Leu Val
1               5                   10

<210> SEQ ID NO 49
<211> LENGTH: 18
<212> TYPE: PRT
<213> ORGANISM: Bovine

<400> SEQUENCE: 49

Asp Asn Pro Gln Val Ser Val Pro Phe Glu Leu Gln Trp Met Leu Ile
1               5                   10                  15

His Cys

<210> SEQ ID NO 50
<211> LENGTH: 9
<212> TYPE: PRT
<213> ORGANISM: Bovine

<400> SEQUENCE: 50

Glu Leu Gln Trp Met Leu Ile His Cys
1               5

<210> SEQ ID NO 51
<211> LENGTH: 16
<212> TYPE: PRT
<213> ORGANISM: Bovine
```

```
<400> SEQUENCE: 51

Phe Pro Val Asn Ser Asn Ser Asn Gly Glu Asn Glu Leu Cys Pro Lys
1               5                   10                  15

<210> SEQ ID NO 52
<211> LENGTH: 14
<212> TYPE: PRT
<213> ORGANISM: Bovine

<400> SEQUENCE: 52

Val Asn Ser Asn Ser Asn Gly Glu Asn Glu Leu Cys Pro Lys
1               5                   10

<210> SEQ ID NO 53
<211> LENGTH: 12
<212> TYPE: PRT
<213> ORGANISM: Bovine

<400> SEQUENCE: 53

Ser Asn Ser Asn Gly Glu Asn Glu Leu Cys Pro Lys
1               5                   10

<210> SEQ ID NO 54
<211> LENGTH: 24
<212> TYPE: PRT
<213> ORGANISM: Bovine

<400> SEQUENCE: 54

Gly Leu Asp Gly Ser Leu Gln Thr Ala Ala Phe Ser Asn Leu Pro Ser
1               5                   10                  15

Leu Phe Asp Ser Gln Trp His Lys
            20

<210> SEQ ID NO 55
<211> LENGTH: 15
<212> TYPE: PRT
<213> ORGANISM: Bovine

<400> SEQUENCE: 55

Ala Ile Gln Arg Val Val Gly Ser Thr Ala Leu Gln Val Ala Tyr
1               5                   10                  15

<210> SEQ ID NO 56
<211> LENGTH: 10
<212> TYPE: PRT
<213> ORGANISM: Human

<400> SEQUENCE: 56

Glu Leu Cys Pro Lys Ile Arg Ile Gly Gln
1               5                   10

<210> SEQ ID NO 57
<211> LENGTH: 8
<212> TYPE: PRT
<213> ORGANISM: Human

<400> SEQUENCE: 57

Asp Leu Ile Ser Gln Phe Gln Val
1               5

<210> SEQ ID NO 58
<211> LENGTH: 12
<212> TYPE: PRT
<213> ORGANISM: Human
```

```
<400> SEQUENCE: 58

Asp Ile Asp Gly Phe Ala Val Leu Gly Lys Leu Ala
1               5                   10

<210> SEQ ID NO 59
<211> LENGTH: 10
<212> TYPE: PRT
<213> ORGANISM: Human

<400> SEQUENCE: 59

Asp Gly Phe Ala Val Leu Gly Lys Leu Ala
1               5                   10

<210> SEQ ID NO 60
<211> LENGTH: 9
<212> TYPE: PRT
<213> ORGANISM: Human

<400> SEQUENCE: 60

Asp Asn Pro Gln Val Ser Val Pro Phe
1               5

<210> SEQ ID NO 61
<211> LENGTH: 18
<212> TYPE: PRT
<213> ORGANISM: Human

<400> SEQUENCE: 61

Asp Asn Pro Gln Val Ser Val Pro Phe Glu Leu Gln Trp Met Leu Ile
1               5                   10                  15

His Cys

<210> SEQ ID NO 62
<211> LENGTH: 9
<212> TYPE: PRT
<213> ORGANISM: Human

<400> SEQUENCE: 62

Glu Leu Gln Trp Met Leu Ile His Cys
1               5
```

DIAGNOSIS OF COLLAGEN IX DESTRUCTION

CROSS-REFERENCE TO RELATED APPLICATIONS

This application is a divisional application of U.S. patent application Ser. No. 12/072,428, filed Feb. 26, 2008, now U.S. Pat. No. 7,892,768, which claims priority from U.S. provisional application Ser. No. 60/904,684 filed Mar. 2, 2007.

FIELD OF THE INVENTION

The present invention relates to methods directed to detecting or monitoring disorders affecting connective tissues, such as joint disease particularly, osteoarthritis, rheumatoid arthritis, reactive arthritis, tendon rupture, osteoporosis, osteomalacia, fracture repair and arteriosclerosis, by determining the levels of cleaved fragments of collagen IX, mediated by IL-1, in serum and synovial fluids. More specifically, the present invention is related to detecting or monitoring the presence of protein fragments, cleaved at novel cleaving sites near the N-terminal part of the collagen IX alpha 1 chain or more specifically close to the C-terminal part of the NC4 domain, and at the COL3 domain close to the NC3 domain. The invention also discloses neoepitope antibodies against the neoepitopes created by the cleavages and an epitope in the cleaved N-terminal part of the NC4 domain unique to collagen IX. A diagnostic kit and antibodies useful in carrying out such methods are also presented.

BACKGROUND

In hyaline cartilage type IX collagen there is a minor constituent of the fiber network having type II collagen as a major constituent. The type IX collagen molecule is a heterotrimer consisting of polypeptide chains α1, α2, and α3 (2). It belongs to the fibril-associated collagens with interrupted triple-helix (FACIT). Each chain contain three triple-helical (collagenous) domains COL 1, 2, and 3 surrounded by four non-triple-helical domains, NC 1, 2, 3, and 4 (3), (see also FIG. 9). The domain numbers are counted from the C-terminal.

Using electron microscopy, it has been shown that type IX collagen decorates the surface of type II collagen fibrils and that the NC 4 domain forms a globular structure, which together with the stalk like COL 3 domain protrudes out from the type II collagen fibril (4).

Type IX collagen is covalently crosslinked to the type II collagen fibrils through binding to both type II collagen and other type IX collagen molecules (5-7). These bonds render extraction of type IX collagen from mature cartilage virtually impossible by agents that do not cleave peptide bonds.

The NC 4 domain has been shown to have an affinity for a number of molecules, for example heparin and cartilage oligomeric matrix protein (COMP) (8-10), whereas COL domains interacts with matrilin-3 (11). Mutations in the interactive COMP, MATN-3, and COL9 have been found in patients with multiple epiphyseal dysplasia, a rare inherited heterogeneous range of diseases, affecting growth and ossification of the epiphysis (12).

NC4-fragments have now surprisingly been shown to be biomarkers for cartilage destruction. The cleavage occurs after aggrecan, a major structural component of cartilage is released, and prior to the major collagen degradation. NC4-fragments are markers of the process leading to destruction before the "point of no return" in contrast to collagen-markers that are like x-rays observations a result of the late stages of the destruction process. Aggrecan-related markers are released in an early stage of the degradation progress and also during normal adaptation of the tissue and therefore do not specifically represent a pathological process. Furthermore aggrecan markers are often associated to inflammation.

After the cleavage of NC4, described in this invention, the large part of type IX collagen that remains crosslinked to type II collagen is potentially further cleaved and released at a later stage. The neoepitope antibody disclosed in the invention herein, against the new C-terminal of the released fragment could detect such cleavage. Additionally, neoepitope antiserum disclosed in the invention, could be used in immunohistochemistry to determine were in the cartilage (superficial—deep, pericellular—interterritorial) the novel cleavage reported here has occurred. An antibody to the newly formed N-terminal of the fragment initially remaining in the tissue could detect a later stage release of such fragments. Additional information on timing could be obtained using the neoepitopes created by cleavage in the col3 domain. A number of earlier publications and patent-applications describe monoclonal antibodies that bind specifically to Type IX collagen, but none of them mentions neoepitope antibodies specifically against cleavage sites near NC4.

Patent application WO1990008195 A1 discloses oligopeptides corresponding to segments of human Type IX collagen useful as antigens in producing monoclonal antibodies which bind immunologically to human Type IX collagen and fragments derived from it. However the segments mentioned in the patent application are not involved in pathological destruction of collagen IX, and therefore not expected in connection to arthritis.

In WO2004110475 A1, assigned, Inst of Nutraceutical Research PTY, the invention relates to compositions comprising the NC4 domain, for treatment and tolerance induction to individuals with symptoms of arthritis. The inventors are also describing methods for recovering polypeptides from connective tissue, having anti-arthritic or anti-inflammatory activity. As in the above-mentioned patent-application the antibody is against uncleaved Collagen IX and not a neoepitope antibody. Furthermore the applicants do not mention NC4 as a marker for diagnosis.

The patent-application WO1999021011 A1, assigned Fibrogen Inc, reveals a method for detecting or monitoring autoimmune disorders and connective tissue disorders by determining the levels of type IX collagen in serum. When preparing antibodies against type IX collagen a sequence in the N-terminal portion of the NC4 domain was selected. This antibody is against uncleaved Collagen IX and not to unique cleavage neoepitopes like in the invention herein.

None of the previous documents describes a specific cleavage site occurring in the NC-4 domain leading to exclusive release of this domain. Although the fact that tissues are completely destroyed in certain diseases, the character of the cleavage cannot be inferred or predicted. It was also unexpected that the cleavage of the molecule in bovine cartilage and human cartilage is different, particularly in view of the sequence similarities (FIG. 10).

Thus, the discovery of specific cleavage sites is novel and opens up for the new diagnostic inventions.

Therefore we have developed a sensitive Western blot technique and a sensitive inhibition ELISA as methods for the identified novel cleavage site facilitating analysis of collagen IX destruction in any human sample, such as synovial fluid, serum, urine and any body fluids. This kind of assay could be used to establish if and when the identified cleavage appear in cartilage degradation and joint deterioration in patients. By using the specific neoepitope antibody of the invention herein, the assay can be used for diagnosis of disease progression and monitoring disease response of treatment. For example to determine the optimal moment for a sportsman with a healing bone fracture to return to the training program.

SUMMARY OF THE INVENTION

Interleukin-1 induced bovine nasal cartilage degradation was used to study catabolic events in the tissue over a 16-day period. Culture medium was fractionated by 2D-electrophoresis (isoelectric focusing and SDS PAGE). Identification of components by peptide mass fingerprinting revealed release of protein fragments such as the NC4 domain of the type IX collagen α1 chain at days 12 and 16.

A novel peptide antibody against an epitope in the N-terminal part of the NC4 domain confirmed the finding and indicated the presence of one of the fragments already at day 9.

Mass spectrometric analysis of the two most abundant fragments revealed that the smallest fragment contained almost the entire NC4 domain, cleaved between arginine-258 and isoleucine-259 in the sequence gives a C-terminal end: ETCNELPAR- (SEQ ID NO: 1) and a N-terminal end: -ITPGARSP (SEQ ID NO: 2) (ETCNELPAR$^{258}$-COOH and NH$_2$-ITPGARSP).

A larger fragment contained the NC4 domain and the COL3 domain with a cleavage site located between glycine-400 and threonine-401 in COL3 gives a C-terminal end: RGPPGPPGPPGPSG- (SEQ ID NO: 3) and a N-terminal end: -TIGFHDGD (SEQ ID NO:4) (RGPPGPPGP-PGPSG$^{400}$-COOH and —NH$_2$-TIGFHDGD) close to the NC3 domain. Presence of multiple collagen α1 (IX) N-terminal sequences demonstrate that the released molecules are cleaved at sites very close to the original N-terminal, either prior to or due to IL-1 treatment.

It has been shown (1) that matrix metalloproteinase 13 (MMP-13) is active and cleaves fibromodulin in this time interval. Cartilage explants treated with MMP-13 were shown to release collagen α1 (IX) fragments with the same sizes and with the same cleavage sites as those obtained upon IL-1 treatment. The presented data describe a potentially important degradation event apparently involving MMP-13 and that precedes the final type II collagen loss.

Further studies of cleavage of collagen IX in human cartilage, revealed that there was specific cleavage sites also of the human collagen IX α1 chain in the NC-4 domain but this surprisingly occurred at a site different from that of the bovine collagen. Cleavage in the site between glutamine-263 and threonine-264 in the CHELPARITPSQTTDERGPP (SEQ ID NO:5); of the human collagen IX alpha 1 chain in the NC-4 domain gives a C-terminal end: CHELPARITPSQ- (SEQ ID NO: 6) and a N-terminal end: -TTDERGPP) (SEQ ID NO: 7). (-CHELPARITPSQ$^{263}$—COOH and NH$_2$-TTDERGPP). The larger fragment, representing the site in the COL3 domain, is of the same size derived from bovine and human cartilage and cleavage occur at the same site between G400 and T401 despite that the S399 in the bovine is exchanged for R399 in the human RGPPGPPGPPGPRG$^{400}$ TIGFHDGD$^{408}$ (SEQ ID NO:8). The cleavage of the human RGPPGPPGP-PGPRG$^{400}$ TIGFHDGD$^{408}$ (SEQ ID NO:8), results in two neoepitopes RGPPGPPGPPGPRG (SEQ ID NO:9) and TIG-FHDGD$^{408}$ (SEQ ID NO:10). The antibodies to all the new neo-epitope ends of the human NC-4 and COL3 ware developed, using standard methods, and showed specific reactivity with the cleavage fragment. The antibodies were used to develop ELISAs for the detection of the epitopes. These ELISAs were used to show presence of the epitopes in synovial fluid from patients with disorders affecting connective tissues, such as joint disease particularly osteoarthritis and rheumatoid arthritis, tendon rupture, fracture repair and arteriosclerosis. The features of the present invention will be more clearly understood by reference to the following examples, which are not to be construed as limiting the invention.

B) Is a graph showing Western blot of synovial fluid samples from patients with joint disease by SDS-polyacrylamide electrophoresis on 4-16% gels followed by electrophoretic transfer to a nitrocellulose membrane add staining with the antibody raised against the PARITPSQ (SEQ ID NO:13) cleavage neoepitope. Bound IgG was detected using a peroxidase conjugated anti-rabbit IgG antibody. Note the presence of a 20 kDa fragment in select synovial fluids containing the neoepitope. The fragment is somewhat smaller than the one released from articular cartilage upon MMP-13 digestion.

Figure 9:
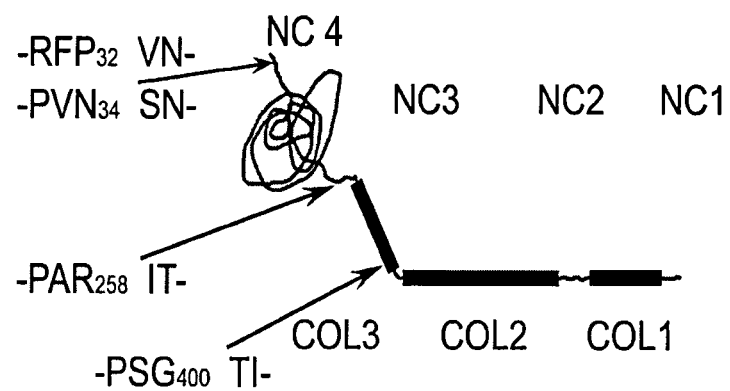

FIG. 9. Is a schematic picture of the type IX collagen molecule with indicated cleavage sites. The thin line represents the non-collagenous domains (NC) and the thick line represents the collagenous domains (COL). The arrows indicate the position of cleavage sites identified and described.

FIG. 10. Cleavage sequences of collagen IX in human and bovine cartilage, respectively.

Figure 1:
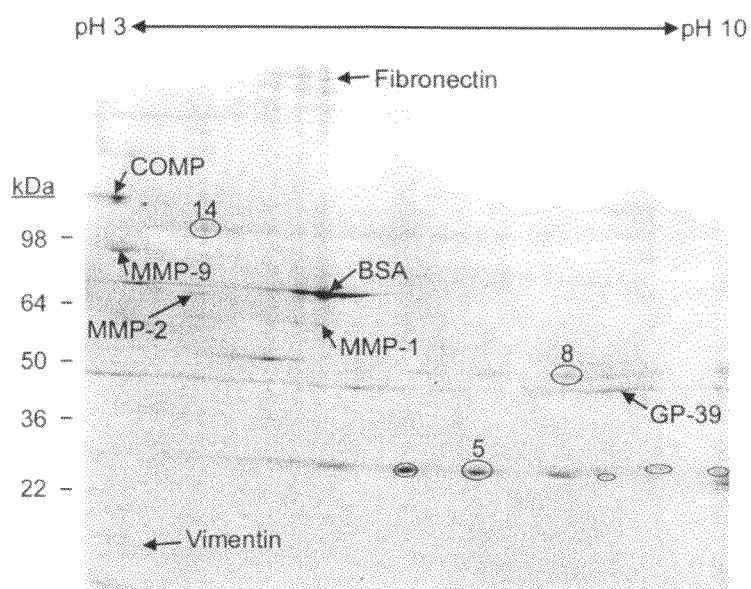
FIG. 1. Shows proteins from IL-1 stimulated bovine nasal cartilage medium day 16 separated using 2D SDS PAGE. The first dimension, isoelectric focusing, was over a pH range 3-10, and the second dimension utilized a 4-20% gradient gel. The numbers to the left of the picture represents the positions of reference marker proteins. Spots marked with rings show those that have been identified as collagen α1 (IX). The different type IX collagen fragments are in the text referred to as the 28 kDa fragment, the 50 kDa fragment, and 100 kDa. In the picture examples of specific spots analyzed have been marked 5, 8, and 14. The results from MALDI-TOF MS (Matrix Assisted Laser Desorption Ionization Time Of Flight Mass Spectrometry) of these spots are presented in the FIGS. 11a, b, and c below.

FIG. 11a. Is a table showing the MALDI MS analysis result of spot 5 from the 2D gel in FIG. 1. Database searches using the Mascot Peptide Mass Fingerprint software (Matrix Science Inc, Boston, Mass., USA) identified collagen α1 (IX). Only peptides from the NC4 domain were matched to peaks in the spectrum. The matched peptides are tabulated with start and end position relating to the bovine sequence: gi|119901059. $M_{(expt)}$ is the measured monoisotopic mass of the peptide, H is a hydrogen, "Delta" means the difference between the measured and the theoretically calculated mass of a matching peptide. "Miss" shows how many missed cleavages that are present in a matched peptide sequence. "Sequence" shows the sequence of the matching peptide with one extra amino acid on both the N- and the C-terminal separated with a hyphen. "Modifications" describe modifications in a peptide sequence, required to match it to an $M_{(expt)}$ obtained with mass spectrometry. Allowed modifications (variable) were oxidation of methionines and hydroxylation of proline residues to form hydroxyproline. All cysteine residues were thought to be carbamidomethylated hence they were not listed.

FIG. 11b. Is a table showing the MALDI MS analysis results of spot 8 from the 2D gel in FIG. 1. Subsequent database search using the Mascot Peptide Mass Fingerprint software identified collagen α1 (IX). Peptides in both the NC4 and the COL3 domain matched to peaks in the spectrum. After the analysis of the 50 kDa fragment released from MMP-13 treated cartilage explants (FIG. 4), this spectrum was inspected for the presence of a peak matching the cleavage site peptide. It was also present in these MALDI data (Observed mass=1274.628). The matched peptides are tabulated with start and end position relating to the bovine sequence: gi|119901059. See description in FIG. 11a for table explanation.

FIG. 11c. Is a table showing the MALDI MS analysis results of spot 14 from the 2D gel in FIG. 1. Subsequent database search using the Mascot Peptide Mass Fingerprint software identified collagen α1 (IX). Peptides from NC4, COL3, and COL2 domains matched to peaks in the spectrum. The matched peptides are tabulated with start and end position relating to the bovine sequence: gi|119901059. See description in FIG. 11a for table explanation.

FIG. 12a. Is a table showing peptides matching bovine collagen α1 (IX) according to a database search using Mascot "MSMS Ions search" (Matrix Science Inc. Boston, Mass., USA). The 28 kDa fragment was cut out from a 2D gel, in-gel digested with AspN, and analyzed using the reversed phase nano-LC on-line with ESI-Qtof MS/MS. This represents data from the same experiment as shown FIG. 3. "M(expt)" means the monoisotopic mass of the matching peptide, otherwise the notations are the same as in FIG. 11. Ion score is based on the probability that an observed match is a random hit (41). Higher values indicate a better hit. The matched peptides are tabulated with start and end position relating to the bovine sequence: gi|119901059.

FIG. 12b. Is a table showing absence of putative trypsin generated sites in the AspN digest of the 28 kDa bovine fragment. The same experiment as in FIG. 3 and FIG. 12a, but searching for peptides in the AspN digest matching putative "tryptic" peptides reveals the cleavage site peptide. No other peptides typical for trypsin digestion were identified. The matched peptides are tabulated with start and end position relating to the bovine sequence: gi|119901059.

Figure 7:
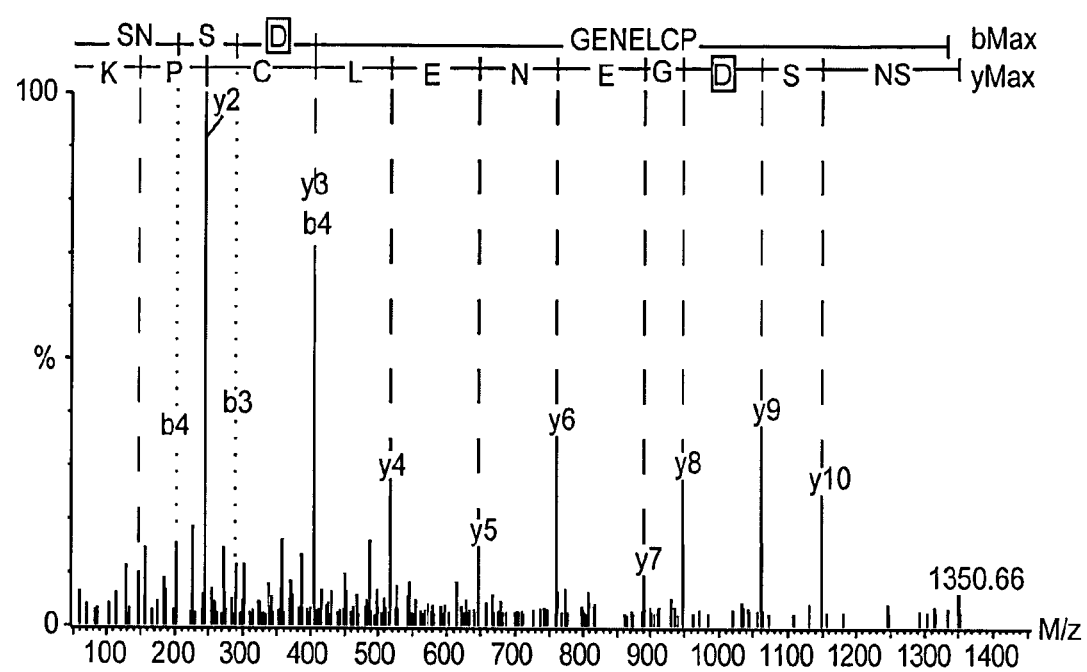
FIG. 7. Shows tandem mass spectrometric data (LC-ESI-QT of MS) of the peptide SNSDGENELCPK (SEQ ID NO:12) in the NC4 domain, that exhibits a non-tryptic N-terminal cleavage. Bands were excised from the gel and digested with trypsin followed by reversed phase chromatography with on-line ESI-Qtof MS. The peptide is deamidated, such that the D (aspartate) in this peptide sequence is an N (asparagine) in the bovine sequence gi|119901059). This annotated spectrum was produced in BioLynx (Peptide sequencing, Waters Djupdalsvägen 12-14 Sollentuna Sweden). The peptide delta mass is 0.01 Da, the average error for y-ions <0.02 Da, and the intensity threshold was set to 2%. From the same experiment as data presented in FIG. 12c.

FIG. 12c. Is a table showing peptides matching bovine collagen α1 (IX) in the 28 kDa band. The 28 kDa band was cut out from a 2D gel, in-gel digested with trypsin, and analyzed using the Qtof setup and data were used to search the NCBI nr database with Mascot "MSMS Ions search". The matched peptides are tabulated with start and end position relating to the bovine sequence: gi|119901059 (FIG. 7). "Modifications" describe modifications in a peptide sequence, required to match it to an m/z obtained with mass spectrometry. Allowed modifications (variable) were oxidation of methionines, deamidation (asparagine and glutamine) and hydroxyprolines. All cysteine residues were thought to be carbamidomethylated, hence they were not listed.

FIG. 13. Is a table showing peptides matching the bovine collagen α1 (IX) chain. The 50 kDa MMP-13 generated sample was cut out from a 1D gel, in-gel digested with trypsin, and analyzed using the reversed phase LC ESI-Ion-Trap MS setup. Data was further analyzed by a database search using Mascot "MSMS Ions search". This was data from the same experiment as FIG. 4b. The matched peptides are tabulated with start and end position relating to the bovine sequence: gi|119901059. See FIGS. 12a and 12c for explanation of the table.

FIG. 14. Is a table showing human peptides matching collagen α1 (IX) in the 30 kDa fragment. Database search result from the IonTrap analysis of the Asp-N digested 30 kDa band originating from the MMP-13 digestion medium separated on α16% SDS PAGE FIG. 15. Is a table showing the "include mass list". Five peptide masses originating from the amino acid sequence of human collagen α1 (IX) NC4 were chosen for MSMS analysis by the reversed phase LC ESI-Qtof MS setup. The two first are the two most C-terminal peptides found in the Asp-N digest of the 30 kDa band of the MMP-13 digestion medium. The third and the fourth were easily detected by the reversed phase LC ESI.IonTrap MS run in parallel and were included as controls. The fifth and last represents the C-terminal peptide expected if the cleavage site would have been the same as in bovine.

DETAILED DESCRIPTION OF THE INVENTION AND PREFERRED EMBODIMENTS THEREOF

Initially bovine work is discussed and further down the details of the invention in humans.

Interleukin-1 induced degradation of bovine nasal cartilage revealed release of fragments, such as the NC4 domain of the type IX collagen α1 chain. The novel peptide antibody of the invention, against the epitope in the N-terminal part of the NC4 domain confirmed the finding.

Mass spectrometric analysis of the two most abundant fragments revealed that the smallest fragment contained almost the entire NC4 domain, cleaved at a novel site between arginine-258 and isoleucine-259 in the sequence ETCNELPAR (SEQ ID NO:1) (-ETCNELPAR$^{258}$—COOH) and -ITPGARSP (SEQ ID NO:2) (NH$_2$-ITPGARSP). A larger fragment contained the NC4 domain and the COL3 domain with a novel cleavage site located between glycine-400 and threonine-401 in COL3, RGPPGPPGPPGPSG- (SEQ ID NO: 3) (RGPP(OH)GP(OH)PGPP(OH)GPSG$^{400}$—COOH) and NH$_2$-TIGFHDGD (SEQ ID NO:4), (NH$_2$-TIGFHDGD-) close to the NC3 domain.

Results of Bovine Study
Bovine Amino Acid Sequence

The amino acid sequence of bovine collagen α1 (IX) that matched to mass spectrometric analysis in this study can be found in the non-redundant (nr) database from "National Center for Biotechnology Information" under the name: gi|119901059 (22 Dec. 2006). Alignment of this sequence from NCBI with the human α1 (IX) sequence (SwissProt P20849 reveals major discrepancies N- and C-terminally (Suppl. 1). The N-terminal part of the bovine sequence is 332 amino acids longer than the human sequence. In this study, no mass spectrometric data matched to any parts of this "additional" sequence. The bovine sequence shows 90% similarity to the first 642 amino acids of the human counterpart, while 279 amino acids in the C-terminal are missing. This bovine sequence is likely to represent an artifact to be replaced. We have therefore chosen to number annotations in this text referring to the human sequence. Database search results maintain their bovine sequence numbers.

Bovine Nasal Cartilage Explant Culture

Proteins released into the medium from IL-1 stimulated cartilage explants (3, 6, 9, 12, and 16 days) were separated using 2D SDS PAGE and identified through peptide mass fingerprinting. Gels from day 3 and day 6 showed irregular separations particularly at the top part, typical of samples containing large amounts of intact and fragmented aggrecan that is too large to enter the gel. In this project focus was on the subsequent degradation after aggrecan release, but before the major collagen release (42). Collagen α1 (IX) was identified at different positions on 2D gels of mediums from day 12 and 16 (a typical gel shown in FIG. 1). The same spots were not present in the control samples incubated without IL-1 (data not shown). A set of faster migrating protein spots had an apparent mass of 28 kDa and the sequence coverage as found by peptide mass fingerprinting (13 peaks matched peptides, FIG. 11a) indicated that they represented a major portion of the NC4 domain of collagen α1 (IX). Peptide mass fingerprinting of the collagen α1 (IX) fragment migrating with an apparent mass of approximately 50 kDa revealed 23 peaks that matched peptides (FIG. 11b), whereof ten were from the COL3 domain and the remaining from NC4. The peptide coverage of the slowest migrating spot identified as collagen α1 (IX) (apparent mass 100 kDa) included in addition to NC4 and COL3, parts of the COL2 domain (25 peaks matched peptides, FIG. 11c). It might represent crosslinked parts or the full size collagen α1 (IX), and was not further studied (the bovine C-terminal sequence not known).

Peptide Antibody

In order to confirm and further enable the study of the identified collagen α1 (IX) fragment, a peptide (NH$_2$-CGQD-DLPGFDLISQFQ$^{64}$—CONH$_2$) (SEQ ID NO:14) from the N-terminal part of the α1 (IX) NC4 domain was synthesized with an added cysteine coupled to Key limpet hemocyanin and used to immunize a rabbit. This NC4-antiserum showed binding to the NC4-peptide in solid state ELISA (titer 1:50000). The binding was inhibited by addition of the NC4-peptide. A peptide concentration of 0.3 ng/ml showed efficient inhibition of the binding.

Western Blot

Figure 2:
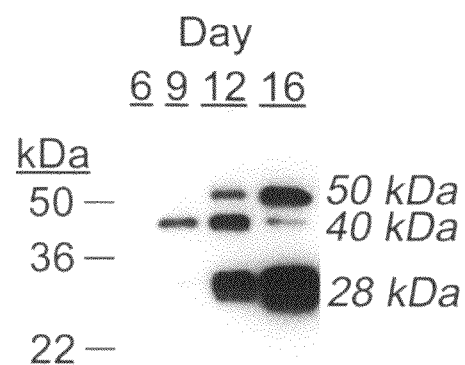
FIG. 2. Shows western blot with the NC4-antiserum of IL-1 stimulated cartilage explants. Medium from day 6, 9, 12, and 16 of IL-1 stimulated cartilage cultures, were separated on 1D SDS PAGE gel. A positive signal at apparent mass of 28 kDa, 40 kDa, and 50 kDa are clearly visible.

Western blots using the polyclonal NC4-antiserum confirmed the presence of collagen α1 (IX) fragments at 28 kDa and 50 kDa in medium from IL-1 stimulated cartilage cultures separated on SDS PAGE. An additional band at a position corresponding to 40 kDa indicated the presence of another collagen α1 (IX) entity initially released somewhat earlier than the other two (FIG. 2). These three fragments are referred to as the 28 kDa, 40 kDa, and 50 kDa fragments respectively.

Identification of Cleavage Sites

Figure 3:
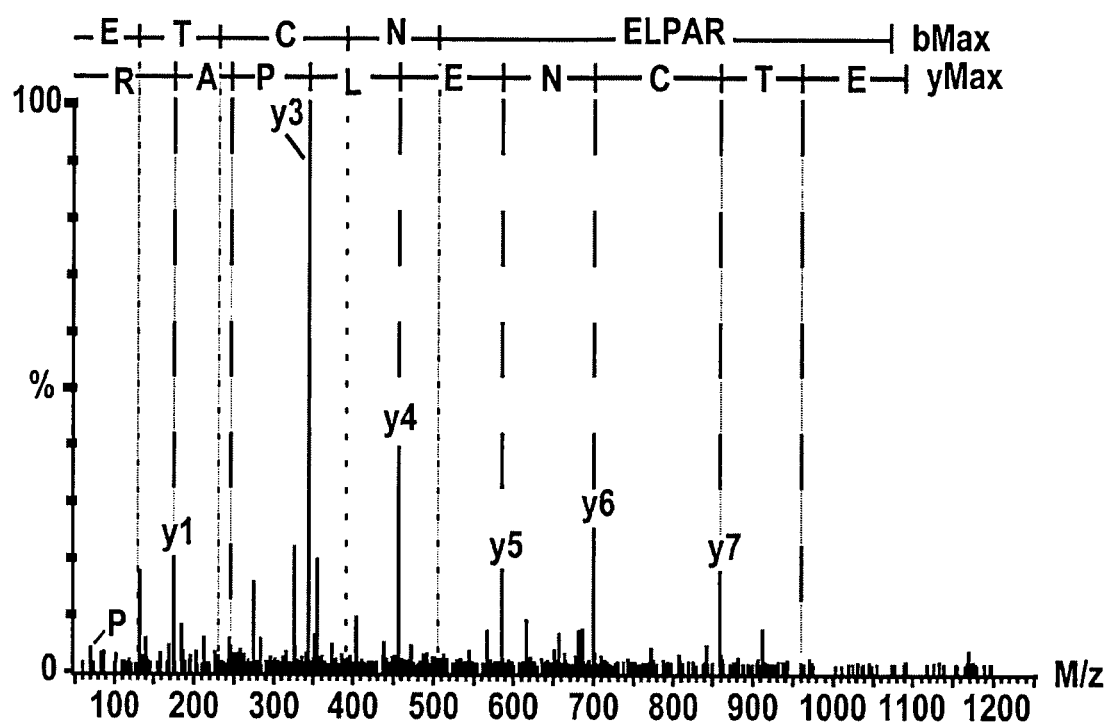
FIG. 3. Shows tandem mass spectrometric data from the most C-terminal peptide of the 28 kDa NC4 fragment. The 28 kDa fragment was in-gel digested with AspN and analyzed with reversed phase LC (liquid chromatography, C18 column) on line with ESI-Qtof MS (ElectroSpray Ionization-Quadrople time of flight mass spectrometry). The deduced peptide sequence is ETCNELPAR (SEQ ID NO:1). The medium from IL-1 stimulated cartilage (day 16) had first been separated on 2D SDS PAGE. This annotated spectrum was produced in the BioLynx software (Peptide sequencing, Waters Djupdalsvägen 12-14 Sollentuna Sweden). The peptide delta mass is <0.01 Da, the average error for y-ions 0.01 Da, and the intensity threshold was set to 0.75%.

The presence of collagen α1 (IX) fragments released into the medium from bovine nasal cartilage stimulated with IL-1 encouraged us to search for cleavage sites. 2D gel pieces containing the 28 kDa fragment were treated with trypsin or AspN prior to LC MSMS (Qtof). Mascot database searches (Matrix Science Inc. Boston Mass., USA) using NCBI non-redundant (nr), carbamidomethyl (C), variable oxidation (M), and variable hydroxylation (P, K) only identified peptides from the NC4 domain. The most C-terminal peptide found in both the trypsin and AspN digested samples was ETCNELPAR$^{258}$ (SEQ ID NO:1) (FIG. 3). This would represent a peptide cleaved correctly at both its terminals by trypsin and a peptide cleaved correctly by AspN at its N-terminal whereas the C-terminal cleavage has to be mediated by another enzyme prior to processing. In FIGS. 2a and 2b peptides matched to MSMS data from the AspN digested sample is tabulated. A Mascot MSMS Ion search for peptides in the AspN digest using trypsin specificity showed only the "cleavage" ETCNELPAR$^{258}$ (SEQ ID NO:1) peptide, demonstrating that there had been no trypsin attack on the identified fragment. Tryptic digests of a 28 kDa spot contained, in addition to other NC4 peptides, three N-terminal peptides, covering amino acids Phe$^{31}$-Lys$^{46}$, Val$^{33}$-Lys$^{46}$, and Ser$^{35}$-Lys$^{46}$ respectively (FIG. 12c and FIG. 7). The two latter, both have non-tryptic cleavages N-terminally, indicating that two new N-terminals are present. Existence of different N-terminals have previously been reported in NC4 isolated after collagenase digestion (43;44), but we observed none of these cleavages in our set of data.

The 50 kDa collagen α1 (IX) fragment was digested in-gel with trypsin and analyzed by reversed phase ESI-IonTrap MS. Nine peptides were sequenced and matched to the NC4-COL3 domains of collagen α1 (IX), whereof the most C-terminal peptide) (RGPP*GPP*GPP*GPSG$^{400}$) (SEQ ID NO:3) had a C-terminal cleavage not generated by the trypsin used (P* denotes hydroxyproline residue. Data not shown).

The minor 40 kDa fragment was identified as collagen α1 (IX) with sequence coverage in the NC4 domain only. It was not further studied.

MMP-13 Digestion of Bovine Nasal Cartilage

Digestion of bovine nasal cartilage with MMP-13 for 24 hours had a visual impact on the cartilage, similar to the IL-1 incubation, such that the tissue started to become transparent. Western blot of the medium using the NC4-antiserum indicated that two collagen α1 (IX) fragments containing the NC4 domain were present. Upon SDS-PAGE, they migrated identically to the 28 kDa and 50 kDa fragments, as demonstrated by Western blot using the anti NC4 peptide-antiserum (FIG. 4a). Upon long exposure, also a weak 40 kDa band appeared, similar to the one found in medium from IL-1 treated cartilage (FIG. 4a inset). The gel pieces with the two bands at 28 kDa and 50 kDa from a Coomassie stained gel were digested with AspN and trypsin, respectively. Analysis by reversed phase LC ESI-IonTrap MS identified N-terminal fragments of collagen α1 (IX). The most C-terminal peptide found in the 28 kDa fragment was ETCNELPAR$^{258}$ (SEQ ID NO:1), the same peptide as in IL-1 stimulated bovine cartilage medium samples from day 12 and 16 (FIG. 3). The peptides identified (by reversed phase LC IonTrap MS) for the MMP-13 generated 50 kDa collagen α1 (IX) fragment are listed in FIG. 13. The most C-terminal peptide had a C-terminal cleavage not generated by the trypsin (FIG. 4b), indicating a newly identified cleavage site. The same peptide was detected in the sample of IL-1 treated cartilage (data not shown), in addition to another COL 3-domain peptide (the same m/z, charge state, and retention time was found in the MMP-13 sample, but no MSMS was performed).

Discussion

This model of tissue breakdown in joint disease where cartilage degradation is induced by IL-1 stimulation has been frequently used in studies of fragmentation and release of tissue macromolecules. It has been shown that aggrecan fragments are initially released, followed by COMP, Fibromodulin, and last collagen (45-47). In medium from cartilage cultured in the presence of IL-1 we found, using 2D gel electrophoresis followed by MALDI MS, release of collagen α1 (IX) fragments. The most abundant fragment detected on 2D gels, with an apparent MW of 28 kDa, represented large parts of the globular NC4 domain. The trailing of the 28 kDa fragment spots on 2D gel over a large interval of isoelectric points, might be due to deamidation of asparagine residues (48). Indeed one of the peptides sequenced appeared to exhibit deamidation (FIG. 7). This phenomenon was not further investigated. The larger 50 kDa fragment was shown to contain NC4 as well as large parts of the COL3 domain.

While type IX collagen domains COL 1, 2, NC 1, and 2 are tightly associated with the type II collagen fibril, COL 3 and the globular NC4 protrude out from the fiber surface (49). This part of the type IX collagen may serve a role as a connector between type II fibrils and other extracellular structural entities. In support, it was recently shown that the absence of type IX collagen could make the cartilage more vulnerable to an autoimmune attack by pathogenic antibodies (50) and reduce its ability to retain matrilin-3 (51). Fragmentation of type IX collagen and loss of the functional NC4 domain from the tissue might thus reflect an important and early step in the process of dismantling cartilage.

The collagen α1 (IX) peptide antibody, as described above, was raised against the synthetic peptide (C)GQDDLPG-FDLISQFQ$^{64}$ (SEQ ID NO:14) representing a sequence close to the N-terminal of the NC4 domain. The peptide was chosen to be C-terminal of one previously used as the immunogen for an antibody against the NC4 domain (52) since these authors described the existence of multiple N-terminals, where some were located in the immunogen sequence they used. Their antibody has been used to describe changes of type IX collagen particularly in the growth plate (53-56). Our mass spectrometry data also demonstrated presence of multiple cleavages at the N-terminal of the NC4 domain (12c and FIG. 7), but none correspond to those previously described. It is not known if these cleavages are the results of IL-1 stimulation or if they are already present in the tissue prior to stimulation.

Western blots with our new NC4-antiserum clearly indicated the presence of three different type IX collagen fragments in medium from day 9, 12, and 16 (FIG. 2). The apparent masses of two of them match earlier identified spots from 2D gels corresponding to approximately 28 kDa and 50 kDa. The third fragment with an apparent mass of 40 kDa was observed already in day 9 medium. Upon trypsin digestion and mass spectrometry of the 40 kDa fragment found in medium from IL-1 stimulated cartilage at day 12, the NC4 domain of collagen α1 (IX) was identified. The apparent mass suggests a fragment larger than the NC4 domain, but data from mass spectrometry shows limited coverage and did not include any peptides from the COL3 domain. The most abundant 28 kDa fragment was selected for more extensive characterization. The larger fragments were expected to be more complex to study due to the collagenous domains and their heterogeneity in hydroxylation of proline residues and the difficulty for enzymes such as trypsin to cleave N-terminally of proline.

Digestion with trypsin and endoprotease AspN combined with reversed phase liquid chromatography on-line with electrospray mass spectrometry (LCMSMS) revealed a neocleavage in the C-terminal part of NC4, a few amino acids N-terminal to the COL 3 domain. The most C-terminal fragment found with trypsin was ETCNELPAR$^{258}$ (SEQ ID NO:1) (I). In order to search for peptides covering parts further to the C-terminal, the NC4 containing fragment was cleaved with AspN. It produced the same most C-terminal peptide ETC-NELPAR$^{258}$ as trypsin, despite that the enzyme will not produce a cleavage between the PAR$^{258}$ and the following isoleucine (FIG. 3). The AspN digest did not contain any other peptides that could have been generated by trypsin, excluding any contamination by this enzyme. As another control, AspN digestion of the longer 50 kDa collagen α1 (IX) fragment did not produce an ETCNELPAR (SEQ ID NO:1) peptide detectable with reversed phase LC ESI-IonTrap MS, whereas trypsin indeed cleaved at the arginine residues to produce this fragment (data not shown). Trypsin digestion of the 50 kDa collagen α1 (IX) fragment, subsequently analyzed by reversed phase LC ESI-IonTrapMS identified two peptides in the COL3 domain in medium from IL-1 day 16. The most C-terminal of them has a C-terminal non-tryptic cleavage (-RGPPGPPGPPGPSG$^{400}$—COOH (SEQ ID NO:3), NH$_2$-TIGFHDGD-) (SEQ ID NO:4), suggesting that this cleavage had occurred in the tissue during IL-1 stimulation (FIG. 13 and FIG. 4b). The 28 kDa and the 50 kDa fragments are released simultaneously from the tissue (FIG. 2) and are thus likely cleaved in parallel, with formation of the 40 kDa fragment preceding.

In previous experiments (57) it was shown that MMP-13 appeared in an active form and cleaved fibromodulin starting around day 9 when cartilage was treated with IL-1. Although the cleavage site in fibromodulin (between -PAY$^{63}$ A$^{64}$YG-) differs from the one found in type IX collagen (-PAR$^{258}$ I$^{259}$ TP-), we decided to test whether digestion of cartilage with MMP-13 could generate the cleavage of collagen α1 (IX) NC4 that we found in medium from IL-1 stimulated cartilage explants.

Bovine nasal cartilage explants were digested with MMP-13 and indeed the enzyme cleaved collagen α1 (IX). The appearance of NC4 containing fragments in the medium as shown by Western blot using the NC4-antiserum was very similar to those from IL-1 induced cleavage (FIG. 4a). The two fragments, 28 kDa and 50 kDa from collagen α1 (IX) NC4 previously observed upon IL-1 stimulation, were released from the bovine cartilage into the medium upon MMP-13 digestion. The 40 kDa band that was seen in IL-1 treated cartilage at day 9, 12, and 16, could be seen as a faint band in this blot upon longer exposure times (FIG. 4a inset). The 28 kDa fragment in medium from MMP-13 digested bovine cartilage was subsequently identified as the NC4 domain of collagen α1 (IX) by reversed phase LC ESI-Ion-Trap MS. It contained the same most C-terminal peptide (ETCNELPAR$^{258}$) (SEQ ID NO:1), as previously found in the medium from IL-1 stimulated bovine cartilage.

The 50 kDa fragment observed in media from both IL-1 stimulated bovine cartilage from day 16 and MMP-13 digested bovine cartilage were shown to contain peptides from the NC4 as well as the COL3 domains. Preliminary analyses of the 50 kDa fragment released both upon IL-1 and MMP-13 treatment of cartilage revealed in both cases the same C-terminal cleavage peptide (R$^{387}$GPP*GPP*GPP*GPSG$^{400}$—COOH (SEQ ID NO:3) with three hydroxylated* residues) generated, in the C-terminal parts of the COL3 domain, prior to our analyses. It is probable that MMP-13 being a collagenase also induced this cleavage also in the IL-1 treated sample. It is likely that the enzyme causing the cleavage in the IL-1 stimulated cartilage indeed is MMP-13, since one substrate site defined represents one for a collagenase and a second is for a different enzyme, such as a gelatinase. MMP-13 represents an enzyme known to have these two activities.

Removal of type IX collagen as a step in tissue maturation has been discussed in earlier studies (58;59). The latter reported that the NC4 domain was removed at the initiation of mineralization, and as the mineralization progressed both type II and IX collagen were removed from the matrix. The cleavage was not identified and it is not possible to conclude whether it was the same as any of those observed here. The presence of MMP-13 in hypertrophic chondrocytes has previously been observed using in situ hybridization (60;61). Combined with the results reported in our present study, it seems plausible that collagen IX is removed from growth plate fibrils by MMP-13, as a step in endochondral bone formation.

The presented data elucidates the degradation of an important cartilage component in a model system and pinpoints MMP-13 as a protease with the ability to accomplish specific cleavages in collagen IX (FIG. 9, 10). Sites of non-triple helix as well as such for triple helical parts were found. The new sites disclosed in the invention, can be used to develop antibodies only recognizing cleaved molecules and could be used in the development of new diagnostics procedures by molecular marker technology.

Results of Human Study

Figure 5:
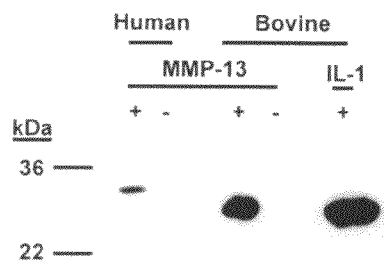
FIG. 5a. Shows western blot, with the NC4 antiserum, of MMP-13 or IL-1 treated human cartilage. Human articular and bovine nasal cartilages were digested with MMP-13 and the latter was also stimulated with IL-1 (day 16). The digest solutions and the medium were separated on a 16% polyacrylamide-SDS gel.
FIG. 5b. Shows tandem mass spectrometric data from the most C-terminal peptide of the human NC4 fragment. The fragment was in-gel digested with Asp-N and analyzed with LC-Qtof MS. Leucine and isoleucine have the exact same mass, thus L in the spectrum represents either L or I. The deduced peptide sequence is ETCHELPARITPSQ (SEQ ID NO:11). The medium from cartilage digested with MMP-13 had been fractionated on a 16% polyacrylamide-SDS gel prior to mass spectrometry.
Figure 5:
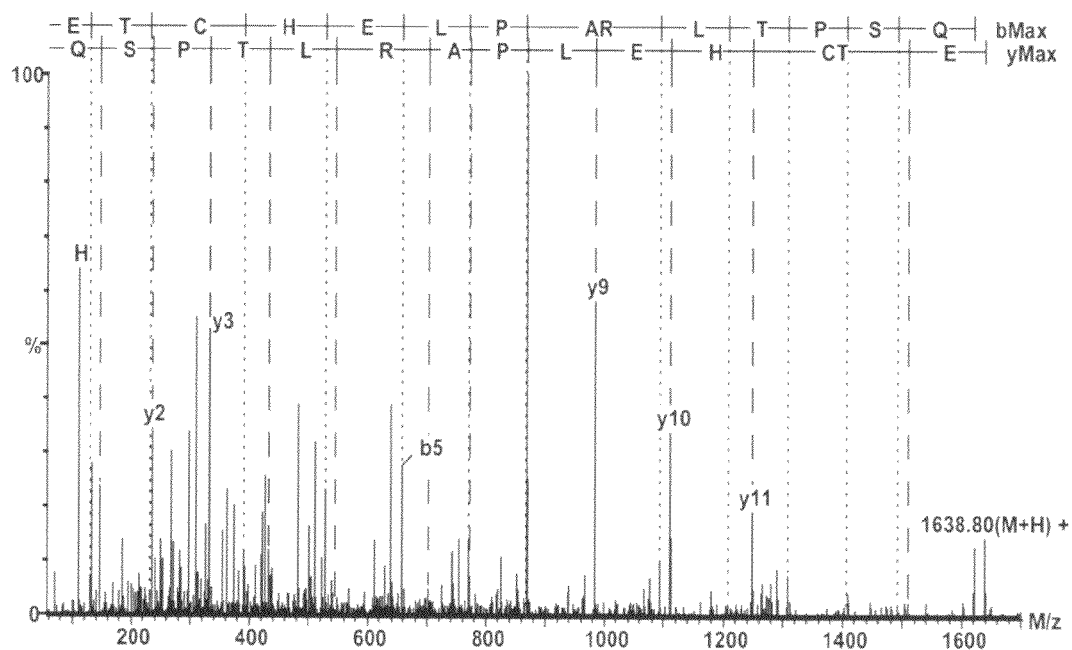

Digestion of Human Articular Cartilage with MMP-13 and Determination of Novel Cleavage Site Human articular cartilage showed no visible signs of degradation upon MMP-13 digestion, in contrast to bovine nasal cartilage. Even so, as the digestion medium was analyzed with Western blots (using the NC4 antiserum) it showed reactivity (FIG. 5a). The band had an apparent mass of 30 kD, which distinguished it from the previously described bovine fragment. A band corresponding to that stained in Western blot was cut out from Coomassie stained gels, digested with Asp-N or Glu-C, and analyzed with reversed phase LC ESI-IonTrap MS. In both digests type IX collagen α1 NC4 was identified (Asp-N result in FIG. 11), as well as a peptide representing a potentially new cleavage site CHEL-PARITPSQ$^{263}$-COOH (SEQ ID NO:6) NH$_2$-TTDERGPP-(SEQ ID NO:7). The new cleavage site is five amino acids C-terminal of the bovine cleavage site, -ETCNELPAR$^{258}$-COOH (SEQ ID NO:1) NH$_2$-ITPGARSP- (SEQ ID NO:2) found in the 28 kD fragment. No masses matching a fragment cleaved at the bovine cleavage site were found in the human sample.

In order to improve and confirm the sequence data of the potential cleavage site peptide, the ESI-Qtof mass spectrometer was used. In our hands the Qtof system is 5× less sensitive compared to the IonTrap, thus three gel bands were pooled and digested with endoproteinase Asp-N in ammonium bicarbonate buffer to yield cleavages N-terminal of aspartic acid (D) and glutamic acid (E).

To avoid that the instrument was occupied running MSMS on an arbitrary peptide eluting prior or at the same time as the potential cleavage site peptide the instrument was set to identify and perform MSMS sequencing on a limited number of peptide masses (FIG. 12). The following peptides were chosen: two internal control NC4 peptides known to elute late, two potential novel cleavage site peptides with zero or one missed Asp-N cleavage, and the human peptide equivalent to the previously identified cleavage site peptide in bovine cartilage. The control peptides and the two potentially novel cleavage site peptides had been detected using ESI-IonTrap mass spectrometry, and we now set out to use ESI-Qtof mass spectrometry to confirm the MSMS data of the two latter peptides. In the Qtof experiment both control peptides and the two peptides originating from the new human cleavage site were sequenced and found to match the type IX sequences (MSMS data from one peptide shown in FIG. 5b). The human peptide equivalent to the bovine cleavage site peptide was not present in the Qtof analyses (nor in IonTrap analysis).

Neoepitope Peptide Antiserum (CPA-antiserum)

Figure 6:
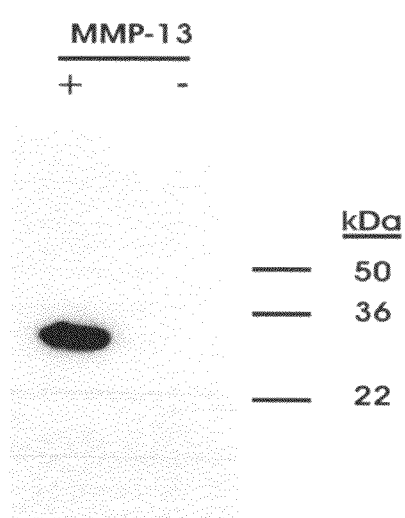
FIG. 6. Shows western blot, using the neoepitope antiserum, of the medium from MMP-13 digested human articular cartilage. Human articular cartilages were digested with MMP-13. The digest solution was separated on a 16% polyacrylamide-SDS gel and electrophoretically transferred to a nitrocellulose membrane, which was incubated with a rabbit antiserum against an internal epitope in NC4 recognizing all variants (right panel) and the neoepitope antibody to PARITPSQ$^{263}$ (SEQ ID NO:13), left panel. Bound antibodies were detected with a peroxidase conjugated anti-rabbit IgG antibodies. The absence of neoepitope reactivity with the larger fragment containing the continuous sequence over the cleavage site demonstrates specificity for the cleaved fragment.
Figure 8:
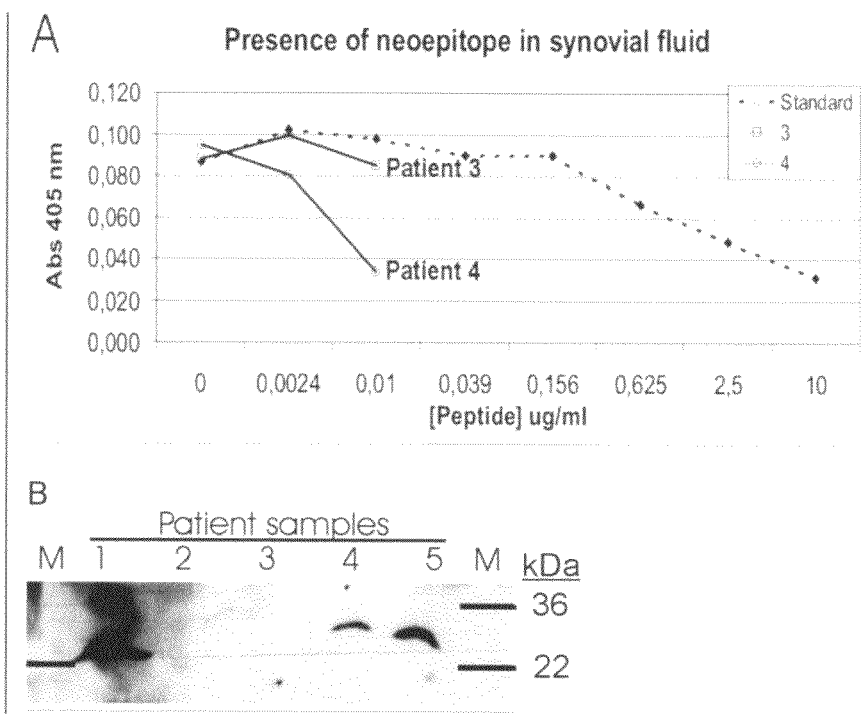
FIG. 8. A) Is a graph showing immunoassay using the neoepitope antiserum, comparing RA and OA samples with and without SDS. Synovial fluid from one RA and one OA patient were analyzed with or without SDS. The samples were diluted 1:10, 1:40, and 1:160.

Western blots of the medium from the human cartilage digested with MMP-13 was performed by separating the digest on 16% SDS PAGE and identification using the neoepitope peptide antiserum. A band at the same position as that observed with the antibody to NC4 was identified (FIG. 6). Synovial fluid from an osteoarthritis patient (in contrast to an rheumatoid arthritis patient) showed strong inhibition in an Inhibition ELISA using the affinity purified CPA-antiserum (FIG. 8). The experiment also showed that the addition of SDS was essential for the synovial fluid epitope to be recognized by the CPA-antiserum.

EXAMPLE 1

Bovine, Collagen α1 (IX) NC4-Peptide Antiserum

A 15-mer peptide sequence of the N-terminal portion of the type IX collagen α1 NC4 domain showing potential as an immunogen and no homology to other sequences found in a BLAST search was selected for immunization. The sequence is identical in human, mouse, rat, cow, chicken, dog, chimpanzee, and rhesus monkey and was represented in medium from IL-1 stimulated cartilage. An N-terminal cysteine was added for coupling, giving the sequence for immunization $NH_2$-CGQDDLPGFDLISQFQ$^{64}$—$CONH_2$ (SEQ ID NO:14). The peptide coupled to Keyhole Limpet Hemocyanin (KLH) was used for immunization of a rabbit. Peptide synthesis and antibody production were custom services provided by Innovagen AB (Lund, Sweden). The peptide and the antiserum will be referred to as NC4-peptide and NC4-antiserum respectively.

EXAMPLE 2

Neoepitope Peptide Antiserum (Human)

The peptide (C)-PARITPSQ$^{263}$—COOH (SEQ ID NO:13), representing the C-terminal part of the released al (IX) fragment, was synthesized, coupled to Keyhole Limpet Hemocyanin (KLH), and used to immunize a rabbit. The antiserum was affinity purified using a column with peptide coupled to agarose. Peptide synthesis, peptide column production and antibody production were custom services provided by Innovagen AB (Lund, Sweden).

EXAMPLE 3

Figure 4:
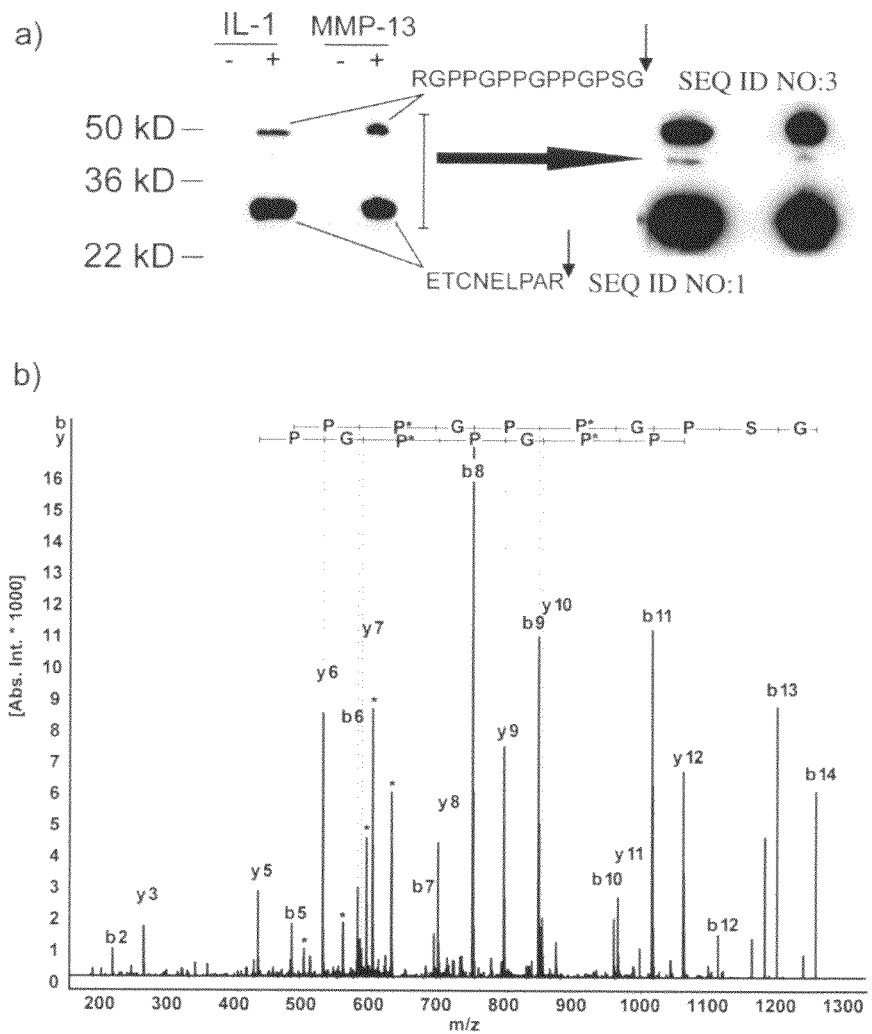
FIG. 4a. Shows western blot of media from IL-1 and MMP-13 treated cartilage using the NC4-antiserum. Proteins released from bovine nasal cartilage treated with IL-1 (day 16) or MMP-13 were separated by 16%-SDS PAGE. The equivalent positions on a Coomassie blue G-250 stained gel were excised, in-gel digested and analyzed with by reversed phase chromatography (C18 column) on line with ESI-Ion-Trap MS (ElectroSpray Ionization Ion Trap mass spectrometry). Both 28 kDa fragments contained the same most C-terminal peptide ETCNELPAR (SEQ ID NO:1) (see FIG. 3). The 50 kDa fragments shared a common most C-terminal peptide RGPP*GPP*GPP*GPSG (SEQ ID NO:3) where P* denotes hydroxyprolines (see FIG. 4b). The insert to the right is an overexposed version of the same blot illustrating the 40 kDa band.
FIG. 4b. Shows tandem mass spectrometry of the most C-terminal peptide in the 50 kDa fragment of bovine collagen IX. Tandem mass spectrometric data from the most C-terminal peptide (RGPP*GPP*GPP*GPSG (SEQ ID NO:3), where P* denotes Hydroxyproline residues) found when the 50 kDa fragment was in-gel digested with trypsin and analyzed with reversed phase chromatography on-line with Ion-Trap MSMS. The MMP-13 digest solution had been separated on 16%-SDS PAGE and stained with Coomassie blue G-250. This annotated spectrum was produced in BioTools (Bruker Daltonics Scandinavia AB, Polygonvägen 79 Täby Sweden). The tolerance error was 0.2 Da, average error for b- and y-ions were 0.06 Da, and the intensity threshold was set to 10.

Western Blot (Bovine)—FIGS. 2,4 and 5a

Samples of medium from bovine cartilage digested with MMP-13 were separated by 16% polyacrylamide-SDS gel electrophoresis and then transferred to a nitrocellulose membrane (Hybond-C, Amersham Biosciences) (38). Blocking was performed overnight with 3% (w/v) low-fat dry milk in Tris-buffered saline (TBS), pH 7.4 and 0.2% (v/v) TWEEN 20™ at 4° C. The membrane was rinsed with the blocking solution (described above) omitting milk and incubated at room temperature with the NC4-antisera diluted 1:1000 in 2% (w/v) milk, TBS, and 0.2% TWEEN 20 for 1 hour. After rinsing, the nitrocellulose membrane was incubated for 1 hour at room temperature with a peroxidase-conjugated secondary antibody diluted 1:30000 (AffiniPure donkey anti-rabbit IgG Jackson ImmunoResearch) in 2% milk/TBS/TWEEN 20. Blots were activated for 1 minute using home made ECL-reagents (20 ml 0.1 M Tris-HCl pH 8.5, 48 µl 250 mM Luminol in DMSO, 48 µl 40 mM p-coumaric acid in DMSO, and 14 µl $H_2O_2$). Agfa CRONEX 5 medical X-ray films were exposed to the membranes for an appropriate time period and automatically developed with an Agfa Curix 60.

EXAMPLE 4

Western Blot (Human)

The affinity purified neoepitope antiserum used in Western blotting of medium from human cartilage digested with MMP-13 was diluted 1:100, while all other conditions are described in example 4.

EXAMPLE 5

Inhibition ELISA

A Nunc Maxisorp (no 446612) was coated with 0.1 µg/ml GGGPARITPSQ$^{263}$—COOH (SEQ ID NO:15) peptide in PBS at room temperature over night in a humid box. Ovalbumin, 2 mg/ml, in PBS was used to block further binding. The peptide standard (0-10 µg/ml) or synovial fluid from osteoarthritis (1:10, 1:40, and 1:160) was dissolved in 0.8% SDS, 0.5% ovalbumin, and 1% pig serum and preincubated on a sterilin plate over night at room temperature in a humid box. Each peptide concentration and synovial fluid dilution was repeated in triplicates. The affinity purified neoepitope antiserum was diluted 1:1000 in 4% triton, 1% pig serum and mixed with the preincubated peptide standard and synovial fluids, prior to transfer to the Nunc plate. Secondary antibody was pig anti rabbit immunoglobulins coupled to alkaline phosphatase (Dako-306) at 1:1000 in 1% pig serum. Para-dinitrophenyl phosphate at 1 mg/ml was used as substrate (9.7% diethanolamine, 0.01% $MgCl_2 \times 6H_2O$, 0.02% $NaN_3$). The absorbance reading at 405 nm was done immediately after substrate addition and then after one hour incubation. The first reading (zero reading) was subtracted from the second reading, the results from three wells treated similarly were averaged, and plotted against peptide concentration or sample dilution.

EXAMPLE 6

Study Comparing the Absence/Presence of NC4 with Bone Mineral Density 5 postmenopausal women with a distal radius fracture, are studied. The patients are treated with a plaster splint for 4 weeks. The bone mineral density (BMD) of the forearm bones is measured with dual-energy x-ray absorptiometry (DEXA) 2, 4, 6 and 8 weeks after the fracture. At the same occasions serum samples are taken. The results of BMD are compared to the presence or absence of NC4 in the serum samples. The detection of NC4 is done according to example 5.

The bone mineral density at fracture site was 28%, 46%, 86%, 103% of the value obtained of the control limb 2, 4, 6 and 8 weeks after the fracture. In all the 5 cases the change of bone mineral density at the fracture site exhibited a correlation with the presence/absence of NC4. At the 2, 4, 6 weeks occasions NC4 is detected while it is absent at the 8 week occasion. The presence/absence of NC4 can accurately determine when the fracture is fully repaired. In conclusion, the amount of NC4 can be used as a new technique in monitoring fracture healing.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents, including functional unimportant variations of sequences, may be resorted to, falling within the scope of the invention, and minor variations are deemed to be equivalent to the particular sequences herein set forth.

Reference List

1. Heathfield, T. F., Önnerfjord, P., Dahlberg, L., and Heinegård, D. (2004) *J. Biol. Chem.* 279, 6286-6295
2. Van der Rest, M., Mayne, R., Ninomiya, Y., Seidah, N. G., Chretien, M., and Olsen, B. R. (1985) *J. Biol. Chem.* 260, 220-225
3. Ninomiya, Y. and Olsen, B. R. (1984) *Proc. Natl. Acad. Sci. USA* 81, 3014-3018
4. Vaughan, L., Mendler, M., Huber, S., Bruckner, P., Winterhalter, K. H., Irwin, M. I., and Mayne, R. (1988) *J. Cell Biol.* 106, 991-997
5. Wu, J. J., Woods, P. E., and Eyre, D. R. (1992) *J. Biol. Chem.* 267, 23007-23014
6. Diab, M., Wu, J. J., and Eyre, D. R. (1996) *Biochem. J.* 314, 327-332
7. Eyre, D. R., Pietka, T., Weis, M. A., and Wu, J. J. (2004) *J. Biol. Chem.* 279, 2568-2574
8. Thur, J., Rosenberg, K., Nitsche, D. P., Pihlajamaa, T., Ala-Kokko, L., Heinegård, D., Paulsson, M., and Maurer, P. (2001) *J. Biol. Chem.* 276, 6083-6092
9. Pihlajamaa, T., Lankinen, H., Ylostalo, J., Valmu, L., Jaalinoja, J., Zaucke, F., Spitznagel, L., Gosling, S., Puustinen, A., Mörgelin, M., Peranen, J., Maurer, P., Ala-Kokko, L., and Kilpelainen, I. (2004) *J. Biol. Chem.* 279, 24265-24273
10. Holden, P., Meadows, R. S., Chapman, K. L., Grant, M. E., Kadler, K. E., and Briggs, M. D. (2001) *J. Biol. Chem.* 276, 6046-6055
11. Budde, B., Blumbach, K., Ylostalo, J., Zaucke, F., Ehlen, H. W., Wagener, R., Ala-Kokko, L., Paulsson, M., Bruckner, P., and Grässel, S. (2005) *Mol. Cell Biol.* 25, 10465-10478
12. Briggs, M. D. and Chapman, K. L. (2002) *Hum. Mutat.* 19, 465-478
13. Fässler, R., Schnegelsberg, P. N. J., Dausman, J., Shinya, T., Muragaki, Y., Mc Carthy, M. T., Olsen, B. R., and Jaenisch, R. (1994) *Proc. Natl. Acad. Sci. USA* 91, 5070-5074
14. Hägg, R., Hedbom, E., Möllers, U., Aszodi, A., Fässler, R., and Bruckner, P. (1997) *J. Biol. Chem.* 272, 20650-20654
15. Neuhold, L. A., Killar, L., Zhao, W. G., Sung, M. L. A., Warner, L., Kulik, J., Turner, J., Wu, W., Billinghurst, C., Meijers, T., Poole, A. R., Babij, P., and DeGennaro, L. J. (2001) *J. Clin. Invest.* 107, 35-44
16. Hu, K., Xu, L., Cao, L., Flahiff, C. M., Brussiau, J., Ho, K., Setton, L. A., Youn, I., Guilak, F., Olsen, B. R., and Li, Y. (2006) *Arthritis Rheum.* 54, 2891-2900
17. Dahlberg, L., Billinghurst, R. C., Manner, P., Nelson, F., Webb, G., Ionescu, M., Reiner, A., Tanzer, M., Zukor, D., Chen, J., van Wart, H. E., and Poole, A. R. (2000) *Arthritis Rheum.* 43, 673-682
18. Mitchell, P. G., Magna, H. A., Reeves, L. M., Lopresti-Morrow, L. L., Yocum, S. A., Rosner, P. J., Geoghegan, K. F., and Hambor, J. E. (1996) *J. Clin. Invest.* 97, 761-768
19. Ståhle-Bäckdahl, M., Sandstedt, B., Bruce, K., Lindahl, A., Jimenez, M. G., Vega, J. A., and LopezOtin, C. (1997) *Lab Invest* 76, 717-728
20. Knäuper, V., Cowell, S., Smith, B., LopezOtin, C., Oshea, M., Morris, H., Zardi, L., and Murphy, G. (1997) *J. Biol. Chem.* 272, 7608-7616
21. Knäuper, V., LopezOtin, C., Smith, B., Knight, G., and Murphy, G. (1996) *J. Biol. Chem.* 271, 1544-1550
22. Fosang, A. J., Last, K., Knäuper, V., Murphy, G., and Neame, P. J. (1996) *Febs Letters* 380, 17-20
23. Heathfield, T. F., Önnerfjord, P., Dahlberg, L., and Heinegård, D. (2004) *J. Biol. Chem.* 279, 6286-6295
24. Deng, S. J., Bickett, D. M., Mitchell, J. L., Lambert, M. H., Blackburn, R. K., Carter, H. L., Neugebauer, J., Pahel, G., Weiner, M. P., and Moss, M. L. (2000) *J. Biol. Chem.* 275, 31422-31427
25. Monfort, J., Tardif, G., Reboul, P., Mineau, F., Roughley, P., Pelletier, J. P., and Martel-Pelletier, J. (2006) *Arthritis Res. Ther.* 8,
26. Leeman, M. F., Curran, S., and Murray, G. I. (2002) *Crit. Rev. Biochem. Mol. Biol.* 37, 149-166
27. Saklatvala, J. (1986) *Nature* 322, 547-549
28. Saklatvala, J., Pilsworth, L. M. C., Sarsfield, S. J., Gavrilovic, J., and Heath, J. K. (1984) *Biochem. J.* 224, 461-466
29. Saklatvala, J., Curry, V. A., and Sarsfield, S. J. (1983) *Biochem. J.* 215, 385-392
30. Borden, P., Solymar, D., Sucharczuk, A., Lindman, B., Cannon, P., and Heller, R. A. (1996) *J. Biol. Chem.* 271, 23577-23581
31. Saxne, T., Di Giovine, F. S., Heinegård, D., Duff, G. W., and Wollheim, F. A. (1988) *J. Autoimmun.* 1, 373-380
32. Saxne, T., Palladino, M. A., Heinegård, D., Talal, N., and Wollheim, F. A. (1988) *Arthritis Rheum.* 31, 1041-1045
33. Heathfield, T. F., Önnerfjord, P., Dahlberg, L., and Heinegård, D. (2004) *J. Biol. Chem.* 279, 6286-6295
34. Heathfield, T. F., Önnerfjord, P., Dahlberg, L., and Heinegård, D. (2004) *J. Biol. Chem.* 279, 6286-6295
35. Laemmli, U. K. (1970) *Nature* 227, 680-685
36. O'Farrell, P. H. (1975) *J. Biol. Chem.* 250, 4007-4021
37. Neuhoff, V., Arold; N., Taube, D., and Ehrhardt, W. (1988) *Electrophoresis* 9, 255-262
38. Towbin, H., Staehelin, T., and Gordon, J. (1979) *Proc. Natl. Acad. Sci. USA* 76, 4350-4354
39. Lorenzo, P., Aspberg, A., Önnerfjord, P., Bayliss, M. T., Neame, P. J., and Heinegård, D. (2001) *J. Biol. Chem.* 276, 12201-12211
40. Rappsilber, J., Ishihama, Y., and Mann, M. (2003) *Anal. Chem.* 75, 663-670
41. Perkins, D. N., Pappin, D. J. C., Creasy, D. M., and Cottrell, J. S. (1999) *Electrophoresis* 20, 3551-3567
42. Heathfield, T. F., Önnerfjord, P., Dahlberg, L., and Heinegård, D. (2004) *J. Biol. Chem.* 279, 6286-6295
43. Vasios, G., Nishimura, I., Konomi, H., Van der Rest, M., Ninomiya, Y., and Olsen, B. R. (1988) *J. Biol. Chem.* 263, 2324-2329
44. Mwale, F., Billinghurst, C., Wu, W., Alini, M., Webber, C., Reiner, A., Ionescu, M., Poole, J., and Poole, A. R. (2000) *Dev. Dyn.* 218, 648-662
45. Heathfield, T. F., Önnerfjord, P., Dahlberg, L, and Heinegård, D. (2004) *J. Biol. Chem.* 279, 6286-6295

46. Goldberg, R. L., Spirito, S., Doughty, J. R., Ganu, V., and Heinegård, D. (1995) *Orthopedic Research Society, 41st Annual Meeting*, 1995, Orlando, Fla. 125-21
47. Sztrolovics, R., White, R. J., Poole, A. R., Mort, J. S., and Roughley, P. J. (1999) *Biochem. J.* 339, 571-577
48. Sarioglu, H., Lottspeich, F., Walk, T., Jung, G., and Eckerskorn, C. (2000) *Electrophoresis* 21, 2209-2218
49. Vaughan, L., Mendler, M., Huber, S., Bruckner, P., Winterhalter, K. H., Irwin, M. I., and Mayne, R. (1988) *J. Cell Biol.* 106, 991-997
50. Carlsen, S., Nandakumar, K., and Holmdahl, R. (2006) *Arthritis Res. Ther.* 8, R102
51. Budde, B., Blumbach, K., Ylostalo, J., Zaucke, F., Ehlen, H. W., Wagener, R., Ala-Kokko, L., Paulsson, M., Bruckner, P., and Grässel, S. (2005) *Mol. Cell Biol.* 25, 10465-10478
52. Mwale, F., Billinghurst, C., Wu, W., Alini, M., Webber, C., Reiner, A., Ionescu, M., Poole, J., and Poole, A. R. (2000) *Dev. Dyn.* 218, 648-662
53. Aurich, M., Mwale, F., Reiner, A., Mollenhauer, J. A., Anders, J. O., Fuhrmann, R. A., Kuettner, M. E., Poole, A. R., and Cole, A. A. (2006) *Arthritis Rheum.* 54, 244-252
54. Kojima, T., Mwale, F., Yasuda, T., Girard, C., Poole, A. R., and Laverty, S. (2001) *Arthritis Rheum.* 44, 120-127
55. Mwale, F., Billinghurst, C., Wu, W., Alini, M., Webber, C., Reiner, A., Ionescu, M., Poole, J., and Poole, A. R. (2000) *Dev. Dyn.* 218, 648-662
56. Mwale, F., Tchetina, E., Wu, C. W., and Poole, A. R. (2002) *J. Bone Miner. Res.* 17, 275-283
57. Heathfield, T. F., Önnerfjord, P., Dahlberg, L., and Heinegård, D. (2004) *J. Biol. Chem.* 279, 6286-6295
58. Hägg, R., Bruckner, P., and Hedbom, E. (1998) *J. Cell Biol.* 142, 285-294
59. Mwale, F., Billinghurst, C., Wu, W., Alini, M., Webber, C., Reiner, A., Ionescu, M., Poole, J., and Poole, A. R. (2000) *Dev. Dyn.* 218, 648-662
60. Johansson, N., Saarialho-Kere, U., Airola, K., Herva, R., Nissinen, L., Westermarck, J., Vuorio, E., Heino, J., and Kähäri, V. M. (1997) *Dev. Dyn.* 208, 387-397
61. Ståhle-Bäckdahl, M., Sandstedt, B., Bruce, K., Lindahl, A., Jimenez, M. G., Vega, J. A., and Lopez-Otin, C. (1997) *Lab Invest* 76, 717-728
62. Saxne, T., Månsson, B., and Heinegård, D. (2006) Biomarkers for cartilage and bone in rheumatoid arthritis. In Firestein, G. S., Panayi, G. S., and Wollheim, F. A., editors. *Rheumatoid Arthritis New Frontiers in Pathogenesis and Treatment*, Oxford University Press, Oxford

---

What is claimed is:

1. An isolated antibody, comprising an antibody having specific reactivity with a cleavage neoepitope of collagen IX, the neoepitope selected from the group consisting of PARITPSQ (SEQ ID NO: 13), TTDERGPP (SEQ ID NO 7), RGPPGPPGPPGPRG (SEQ ID NO: 9) and TIGFHDGD (SEQ ID NO: 10), wherein the isolated antibody does not react with full length collagen IX and is useful for detection of collagen IX cleavage.

2. A diagnostic kit useful in detecting or monitoring a human disorder affecting connective tissues, comprising an antibody having specific reactivity with a cleavage neoepitope of collagen IX, the neoepitope selected from the group consisting of PARITPSQ (SEQ ID NO: 13), TTDERGPP (SEQ ID NO 7), RGPPGPPGPPGPRG (SEQ ID NO: 9) and TIGFHDGD (SEQ ID NO: 10)), wherein the isolated antibody does not react with full length collagen IX and the diagnostic kit is useful for detection of collagen IX cleavage.

* * * * *